United States Patent
Johnson et al.

(10) Patent No.: US 9,702,870 B2
(45) Date of Patent: Jul. 11, 2017

(54) FLUORESCENT DYES AND RELATED METHODS

(71) Applicant: University of Washington through its Center for Commercialization, Seattle, WA (US)

(72) Inventors: Lewis E. Johnson, Seattle, WA (US); Rose Ann Cattolico, Seattle, WA (US); Bruce H. Robinson, Seattle, WA (US); Luke N. Latimer, Berkeley, CA (US); Zachary H. Watanabe-Gastel, Seattle, WA (US); William Robert Hardin, Seattle, WA (US)

(73) Assignee: University of Washington Through its Center for Commercialization, Seattle, WA (US)

(*) Notice: Subject to any disclaimer, the term of this patent is extended or adjusted under 35 U.S.C. 154(b) by 0 days.

(21) Appl. No.: 15/203,607

(22) Filed: Jul. 6, 2016

(65) Prior Publication Data

US 2016/0313312 A1    Oct. 27, 2016

Related U.S. Application Data

(62) Division of application No. 14/418,303, filed as application No. PCT/US2013/053868 on Aug. 6, 2013, now Pat. No. 9,410,947.

(60) Provisional application No. 61/680,581, filed on Aug. 7, 2012.

(51) Int. Cl.
| | |
|---|---|
| C07D 213/89 | (2006.01) |
| C07D 213/38 | (2006.01) |
| G01N 33/53 | (2006.01) |
| C09B 57/00 | (2006.01) |
| C12Q 1/68 | (2006.01) |
| C09B 57/02 | (2006.01) |
| C09B 69/06 | (2006.01) |
| G01N 33/58 | (2006.01) |
| G01N 1/30 | (2006.01) |
| H01L 51/00 | (2006.01) |

(52) U.S. Cl.
CPC ....... *G01N 33/5308* (2013.01); *C07D 213/38* (2013.01); *C07D 213/89* (2013.01); *C09B 57/00* (2013.01); *C09B 57/008* (2013.01); *C09B 57/02* (2013.01); *C09B 69/06* (2013.01); *C12Q 1/6806* (2013.01); *G01N 1/30* (2013.01); *G01N 33/582* (2013.01); *G01N 2001/302* (2013.01); *H01L 51/0003* (2013.01); *H01L 51/005* (2013.01); *H01L 51/0052* (2013.01); *H01L 51/0067* (2013.01); *H01L 51/0073* (2013.01); *H01L 51/0093* (2013.01)

(58) Field of Classification Search
None
See application file for complete search history.

(56) References Cited

U.S. PATENT DOCUMENTS

| | | | |
|---|---|---|---|
| 4,515,796 A | 5/1985 | Robertson | |
| 2007/0053831 A1 | 3/2007 | Barrio et al. | |
| 2011/0269761 A1 | 11/2011 | Langkopf et al. | |
| 2012/0052506 A1 | 3/2012 | Yue et al. | |

FOREIGN PATENT DOCUMENTS

| | | |
|---|---|---|
| WO | 99/31086 | 6/1999 |
| WO | 2005/040337 | 5/2005 |

OTHER PUBLICATIONS

Verbiest, T.; Clays, K.; Samyn, C.; Wolff, J.; Reinhoudt, D.; Persoons, A., Investigations of the Hyperpolarizabiltiy in Organic Molecules from Dipolar to Octupolar Systems. Journal of the American Chemical Society 1994, 116 (20), 9320-9323.
Kin, B.; Zhang, Y.; Liu, L; Wang, Y., Water-Promoted Suzuki Reaction in Room Temperature Ionic Liquids. Synlett 2005, (20), 3083-3086.
Yanai, T.; Tew, D.P.; Handy, N. C., A new hybrid exchange-correlation functional using the Coulomb-attenuating method (CAM-B3LYP). Chemical Physics Letters 2004,393 (1-3), 51-57.
Zhao, Y.; Truhlar, D. G., The M06 suite of density functionals for main group thermochemistry, thermochemical kinetics, noncovalent interactions, excited states, and transition elements: two new functionals and systematic testing of four M06-class functionals and 12 other functionals. Theoretical Chemistry Accounts 2007, 120 (1-3), 215-241.
Lee et al., "Development of nove cell-permeable DNA sensitive dyes using combinational synthesis and cell based screening" Chem Commun (2003), pp. 1852-1853.
Ephardt et al., 97(17) J. Phys. Chem. 4540-7 (1993) (CAS Abstract).
Reinhardt et al., Proceedings of SPIE—The International Society for Optical Engineering, 3146 Nonlinear Optical Liquids and Power Limiters), 2-11 (1997) (CAS Abstract).
Skofic et al., Zbornik Referatov S Posvetovanja Slovenski Kemijski Dnevi. Maribor, Slovenia, 308-312 Sep. 17-18, 1998 (CAS Abstract).
Angerer, L.M. and E.N. Moudrianakis (1972) "Interaction of ethidium bromide with whole and selectively deproteinized deoxynucleoproteins from calf thymus," J Mol Biol, 63:505-521.
Arvela, R. K.; Leadbeater, N. E., Suzuki Coupling of Aryl Chlorides with Phenylboronic Acid in Water, Using Microwave Heating with Simultaneous Cooling. Organic Letters 2005, 7 (11), 2101-2104.
Atherton, S. J.; Harriman, A., Photochemistry ofintercalated Methylene Blue: Photoinduced Hydrogen Atom Abstraction from Guanine and Adenine. Journal of the American Chemical Society 1993, 115 (5), 1816-1822.
Benight, S. J.; Bale, D. H.; Olbricht, B. C.; Dalton, L. R., Organic electro-optics: Understanding material structure/function relationships and device fabrication issues. Journal of Materials Chemistry 2009, 19 (40), 7466-7475.

(Continued)

*Primary Examiner* — Timothy R Rozof
(74) *Attorney, Agent, or Firm* — McDonnell Boehnen Hulbert & Berghoff LLP

(57) ABSTRACT

Fluorescent dyes with affinity for nucleic acids and related methods are provided. Dielectric or semiconducting films including fluorescent dyes with affinity for nucleic acids and related methods are also provided. Coumarin-based surfactants conjugated to the fluorescent dyes with affinity for nucleic acids and related methods are provided.

10 Claims, 1 Drawing Sheet

(56) References Cited

OTHER PUBLICATIONS

Benight, S. J.; Johnson, L. E.; Barnes, R.; Olbricht, B. C.; Bale, D. H.; Reid, P. J.; Eichinger, B. E.; Dalton, L. R.; Sullivan, P. A.; Robinson, B.H., Reduced Dimensionality in Organic Electro-Optic Materials: Theory and Defined Order. Journal of Physical Chemistry B, 2010, 114 (37), 11949-11956.

Brahadeeswaran, S.; Onduka, S.; Takagi, M.; Takahashi, Y.; Adachi, H.; Kamimura, T.; Yoshimura, M.; Mori, Y.; Yoshida, K.; Sasaki, T., Twin-free and High-Quality DAST Crystals—Effected through Solutions of Lower Supersaturation Coupled with Isothermal Solvent Evaporation. Crystal Growth & Design 2006, 6 (11), 2463-2468.

Chiappe, C.; Piccioli, P.; Pieraccini, D., Selective N-alkylation of anilines in ionic liquids. Green Chemistry 2006, 8 (3), 277.

Clays, K.; Persoons, A., Hyper-Rayleigh scattering in solution. Review of Scientific Instruments 1992, 63 (6), 3285.

Dalton, L. R.; Benight, S. J.; Johnson, L E.; Knorr, D. B.; Kosilkin, I.; Eichinger, B. E.; Robinson, B. H.; Jen, A. K. Y.; Overney, R. M., Systematic Nanoengineering of Soft Matter Organic Electro-optic Materials. Chemistry of Materials 2011, 23 (3), 430-445.

Dalton, L. R.; Harper, A. W.; Robinson, B. H., The role of London forces in defining noncentrosymmetric order of high dipole moment-high hyperpolarizability chromophores in electrically poled polymeric thin films. Proceedings of the National Academy of Sciences 1997, 94, 4842-4847.

Dalton, L. R.; Steier, W. H.; Robinson, B. H.; Zhang, C.; Ren, A.; Garner, S.; Chen, A.; Londergan, T.; Irwin, L; Carlson, B.; Fifield, L; Phelan, G.; Kincaid, C.; Amend, J.; Jen, A., From molecules to opto-chips: organic electro-optic materials. Journal of Materials Chemistry, 1999, 9 (9), 1905-1920.

Del Castillo, P.; Horobin, R. W.; Blaquez-Castro, A.; Stockert, J. C., Binding of cationic dyes to DNA: distinguishing intercalation and groove binding mechanisms using simple experimental and numerical models. Biotechnic & Histochemistry 2010,85 (4), 247-256.

Ephardt, H.; Fromherz, P., Fluorescence of Amphiphilic Hemicyanine Dyes without Free Double Bonds. Journal of Physical Chemistry 1993, 97 (17), 4540-4547.

Fromherz, P., Monopole-Dipole Model for Symmetrical Solvatochromism of Hemicyanine Dyes. Journal of Physical Chemistry 1995, 99 (18), 7188-9192.

Graham, H. W., Gymnodinium Catenatum, A New Dinoflagellate from the Gulf of California. Transactions of the American Microscopical Society 1943, 62 (3), 259-261.

Gromov and Fomina, Reactions of isoquinoline derivatives with pyridinium salts yielding 4-naphthylpyridines, Russian Chemical Bulletin, Apr. 2004, vol. 53, Issue 4, pp. 901-905.

Grote, J. G.; Ogata, N.; Hagen, J. A.; Heckman, E.; Curley, M. J.; Yaney, P. P.; Stone, M.O.; Diggs, D. E.; Nelson, R. L.; Zetts, J. S.; Hopkins, R K; Dalton, L. R., Deoxyribonucleic Acid (DNA) based nonlinear optics. Proceedings of SPIE 2003, 5211, 53-62.

Grote, J.G. et al. (2004) "A Real-Time QCM-D Approach to Monitoring Mammalian DNA Damage Using DNA Adsorbed to a Polyelectrolyte Surface," J Phys Chem B, 108(25):8584-8591.

Heckman, E. M., Poling and optical studies of DNA NLO waveguides. Proceedings of SPIE 2005, 5934, 593408-593408-7.

Heckman, E. M.; Hagen, J. A.; Yaney, P. P.; Grote, J. G.; Hopkins, F. K., Processing techniques for deoxyribonucleic acid: Biopolymer for photonics applications. Applied Physics Letters 2005, 87 (21), 211115.

Heckman, E. M.; Yaney, P. P.; Grote, J. G.; Hopkins, F. K, Development and performance of an all-DNA-based electro-optic waveguide modulator. Proceedings of SPIE, 2006, 6401, 640108-640108-10.

Heckman, E. The Development of an All-DNA-Based Electro-Optic Waveguide Modulator. University of Dayton, Dayton, OH, 2006.

Heckman, E.M. et al. (2006) "Performance of an electro-optic waveguide modulator fabricated using a deoxyribonucleic-acid-based biopolymer," Appl Phys Lett, 89(18):181116.

International Search Report and Written Opinion dated Apr. 16, 2010 for PCT/US2013/053868 filed Aug. 6, 2013.

Johnson, L. E. (2012). Multi-Scale Modeling of Organic Electra-Optic Materials. Doctor of Philosophy, University of Washington, Seattle.

Johnson, L. E., Latimer, L. N., Benight, S. J., Watanabe, L H., Elder, D. L., Robinson, B. H., . . . Clays, K. (2012). Novel cationic dye and crosslinkable surfactant for DNA biophotonics. Proc. SPIE—Nanobiosystems: Processing, Characterization, and Applications V, 8464, 84640D1-84640D10. doi: 10.1117/12.964958.

Leadbeater, N. E.; Williams, V. A.; Barnard, T. M.; Collins, M. J., Open-Vessel Microwave-Promoted Suzuki Reactions Using Low Levels of Palladium Catalyst: Optimization and Scale-Up. Organic Process Research & Development 2006, 10 (4), 833-837.

Liu, L.; Zhang, Y.; Wang, Y., Phosphine-free palladium acetate catalyzed Suzuki reaction in water. Journal of Organic Chemistry 2005, 70 (15), 6122-5.

Luo, J.; Zhou, X.-H.; Jen, A. K. Y., Rational molecular design and supramolecular assembly of highly efficient organic electro-optic materials. Journal of Materials Chemistry, 2009, 19 (40), 7410.

Mitus, A. C.; Pawlik, G.; Kochalska, A.; Mysliwiec, J.; Miniewicz, A.; Kajzar, F., Experimental and Monte Carlo studies of diffraction grating inscription in DNA-based materials. 2007, Proc. SPIE 6646, Nanobiotronics, 664601-664601-8.

Nelson, J. W.; Tinoco, I., Intercalation of Ethidium Ion into DNA and RNA Oligonucleotides. Biopolymers 1984, 23 (2), 213-233.

Nordmeier, E., Absorption spectroscopy and dynamic and static light-scattering studies of ethidium bromide binding to calf thymus DNA: implications for outside-binding and intercalation. The Journal of Physical Chemistry 1992, 96 (14), 6045-6055.

Olbrechts, G.; Wostyn, K.; Clays, K.; Persoons, A., High-frequency demodulation of multiphoton fluorescence in long-wavelength hyper-Rayleigh scattering. Optics Letters 1999, 24 (6), 403-405.

Oudar, J. L; Chemla, D. S., Hyperpolarizabilities of the nitroanilines and their relations to the excited state dipole moment. J Chem Phys 1977, 66 (6), 2664-2668.

Pan, F.; Wong, M.S.; Bosshard, C.; Gunter, P., Crystal Growth and Characterization of the Organic Salt 4-N, N-Dimethylamino-4'-N-methyl-stilbazolium Tosylate (DAST). Advanced Materials 1996, 8 (7), 592-595.

Pawlik, G.; Mitus, A. C.; Mysliwiec, J.; Miniewicz, A.; Grote, J. G., Photochromic dye semi-intercalation into DNA-based polymeric matrix: Computer modeling and experiment. Chemical Physics Letters 2010,484 (4-6), 321-323.

Peacocke, A.R. and J.N. H. Skerrett (1956) "The interaction of aminoacridines with nucleic acids," Trans Faraday Soc, 52:261-279.

Pohl, F. M.; Jovin, T. M.; Baehr, W.; Holbrook, J. 1., Ethidium Bromide as a Cooperative Effector of a DNA Structure. Proceedings of the National Academy of Sciences 1972, 69 (12), 3805-3809.

Press, W. H., Teukolsky, S.A., Vetterling, W.T., Flannery, B.P., Numerical Recipes. 3rd ed.; Cambridge University Press: Cambridge (UK), 2007.

R.J. Rawle, C.R.D. Selassie, M.S. Johal (2007) "A Real-Time QCM-D Approach to Monitoring Mammalian DNA Damage Using DNA Adsorbed to a Polyelectrolyte Surface," Langmuir, 23:9563-9566.

Rice, J. E.; Handy, N., The calculation of frequency-dependent polarizabilities as pseudo-energy derivatives. Journal of Chemical Physics 1991, 94 (7), 4959-4971.

Ruiz, B.; Jazbinsek, M.; Gunter, P., Crystal Growth of DAST. Crystal Growth & Design 2008, 8 (11), 4173-4184.

Samoc, M.; Samoc, A.; Miniewicz, A.; Przemyslaw, M.P.; Prasad, P. N.; Grote, J. G., Cubic nonlinear optical effects in deoxyribonucleic acid (DNA) based materials containing chromophores. 2007, 6646, 66460A-66460A-10.

Scatchard, G. (1949) "The Attractions of Proteins for Small Molecules and Ions," Annals of the New York Academy of Sciences, 51:662-672.

Singer, K. D.; Kuzyk, M.G.; Sohn, J. E., Second-order nonlinear-optical processes in orientationally ordered materials: relationship between molecular and macroscopic properties. Journal of the Optical Society of America B, 1987, 4 (6), 968-976.

(56) References Cited

OTHER PUBLICATIONS

Sommer, H. Z.; Lipp, H. I.; Jackson, L. L., Alkylation of Amines. A General Exhaustive Alkylation Method for the Synthesis of Quaternary Ammonium Compounds. Journal of Organic Chemistry 1971, 36 (6), 824-828.
Stadler, S.; Dietrich, R.; Bourhill, G.; Bdiuchle, C., Long-wavelength first hyperpolarizability measurements by hyper-Rayleigh scattering. Optics Letters 1996, 21(4), 251-253.
Suponitsky, K. Y.; Liao, Y.; Masunov, A. E., Electronic Hyperpolarizabilities for Donor-Acceptor Molecules with Long Conjugated Bridges: Calculations versus Experiment. Journal of Physical Chemistry A 2009, 113 (41), 10994-11001.
Szablewski, M.; Thomas, P.R.; Thornton, A.; Bloor, D.; Cross, G. H.; Cole, J. M.; Howard, J. A. K; Malagoli, M.; Meyers, F.; Bredas, J.-L.; Wenseleers, W.; Goovaerts, E., Highly Dipolar, Optically Nonlinear Adducts of Tetracyano-p-quinodimethane Synthesis, Physical Characterization, and Theoretical Aspects. Journal of the American Chemical Society 1997, 119 (13), 3144-3154.
Tian, Y.; Kong, X.; Nagase, Y.; Iyoda, T., Photocrosslinkable Liquid-Crystalline Block Copolymers with Coumarin Units Synthesized with Atom Transfer Radical Polymerization. Journal of Polymer Science: Part A: Polymer Chemistry 2003, 11, 2197-2206.

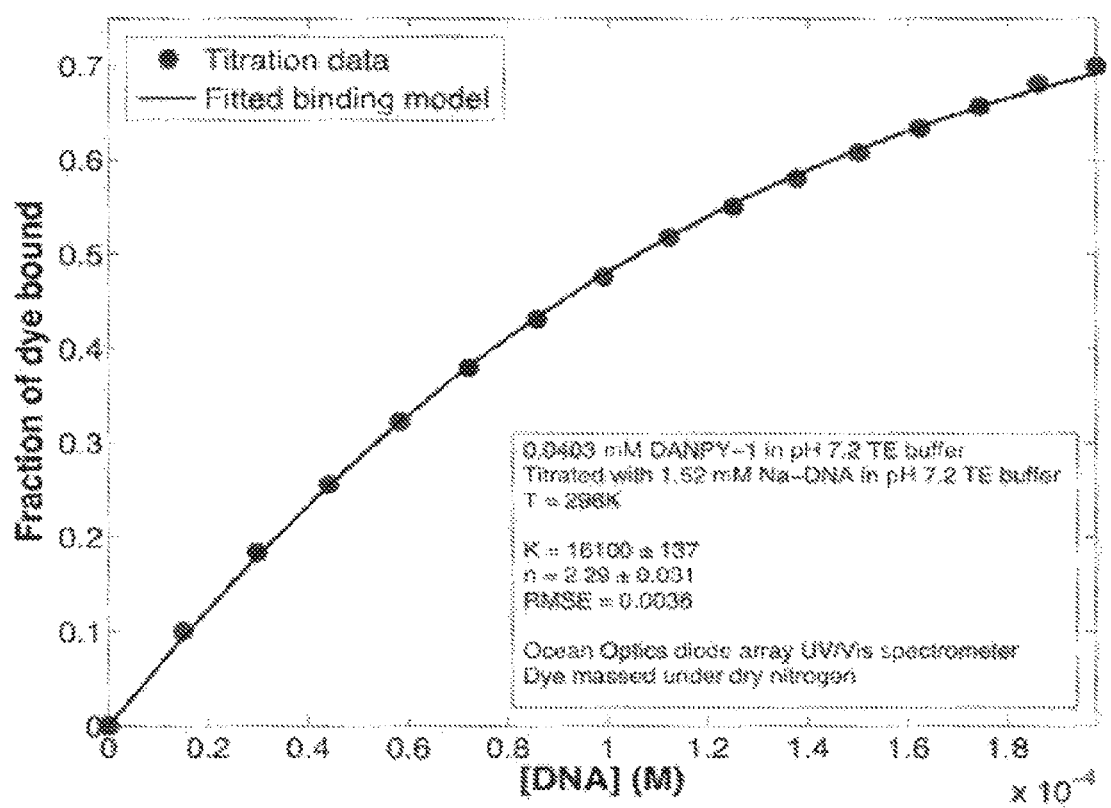

FLUORESCENT DYES AND RELATED METHODS

CROSS-REFERENCE TO RELATED APPLICATIONS

This application is a divisional of U.S. patent application Ser. No. 14/418,303, filed on Jan. 29, 2015, which is a U.S. national phase of International Application No. PCT/US2013/053868, filed on Aug. 6, 2013, which claims priority to U.S. Provisional Application No. 61/680,581, filed Aug. 7, 2012, the disclosures of which are hereby incorporated by reference in their entireties.

STATEMENT AS TO FEDERALLY SPONSORED RESEARCH

This invention was made with government support under FA8650-04-D-1712 awarded by the Air Force Research Laboratory, and DMR-0120967 awarded by the National Science Foundation. The government has certain rights in the invention.

BACKGROUND OF THE INVENTION

Fluorescent compounds capable of interacting with DNA can be used for a variety of applications. For example, fluorescent molecules with an affinity for DNA can be used for identification and separation of subpopulations of cells by flow cytometry, cell sorting, quantification, and/or fluorescence microscopy. In other applications, DNA can be detected by using fluorescent molecules with an affinity for DNA to fluoresce upon binding to DNA molecules in a sample. In addition to serving as fluorescent molecules for detection of DNA, biopolymers such as DNA can be used as a host material for nonlinear optical dyes for photonic applications. In some instances, fluorescent molecules with an affinity for DNA can be integrated into the DNA host material in films for photonic applications. However, dyes can be problematic for integrating into the films and the DNA host material for use in photonic applications. Moreover, fluorescent molecules with an affinity for DNA can suffer from photobleaching and other aspects that may decrease their use as effective dyes for DNA detection.

Thus, there is a need for new compounds that can, e.g., have an affinity for DNA and/or have optical properties suitable for use in films for photonic applications. The present disclosure provides this need and more.

SUMMARY OF THE INVENTION

The present disclosure provides compounds (e.g., fluorescent dyes) having affinity for nucleic acid molecules and/or having optical nonlinearity useful e.g., for a variety of photonic applications. The present disclosure also provides surfactant-compound molecules that can be also, e.g., be used for various applications, such as photonic applications. The present disclosure further includes related methods of using the compounds.

In one aspect, the present disclosure includes a compound having the general formula (I):

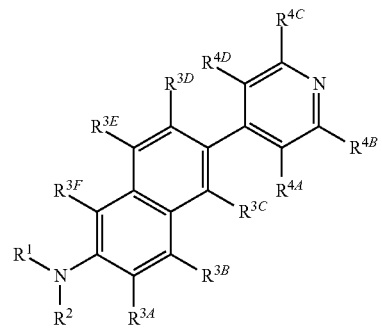

(I)

wherein each of $R^1$ and $R^2$ are independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein $R^1$ and $R^2$ are joined together to form a substituted or unsubstituted cycloalkyl, substituted or unsubstituted heterocycloalkyl, substituted or unsubstituted aryl, or substituted or unsubstituted heteroaryl; each of $R^{3A}$, $R^{3B}$, $R^{3C}$, $R^{3D}$, $R^{3E}$, $R^{3F}$, $R^{4A}$, $R^{4B}$, $R^{4C}$, and $R^{4D}$ are independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl; and salts and isomers thereof.

In another aspect, the present disclosure includes a compound having the general formula (II):

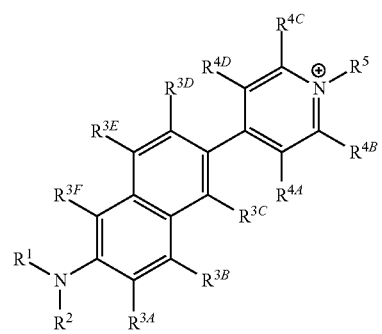

(II)

wherein each of $R^1$ and $R^2$ are independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein $R^1$ and $R^2$ are joined together to form a substituted or unsubstituted cycloalkyl, substituted or unsubstituted heterocycloalkyl, substituted or unsubstituted aryl, or substituted or unsubstituted heteroaryl; each of $R^{3A}$, $R^{3B}$, $R^{3C}$, $R^{3D}$, $R^{3E}$, $R^{3F}$, $R^{4A}$, $R^{4B}$, $R^{4C}$, and $R^{4D}$ are independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl; R$^5$ is selected from the group consisting of a halide, —CN, —NO$_2$, fluorinated alkyl, fluorinated heteroalkyl, fluorinated acyl, fluorinated alkoxy, fluorinated cycloalkyl, fluorinated heterocycloalkyl, fluorinated aryl, fluorinated heteroaryl, unsubstituted alkyl, unsubstituted heteroalkyl, unsubstituted acyl, unsubstituted alkoxy, unsubstituted cycloalkyl, unsubstituted heterocycloalkyl, unsubstituted aryl, and unsubstituted heteroaryl; and salts and isomers thereof.

In yet another aspect, the present disclosure includes a method for detecting a nucleic acid molecule in a sample. The method can include combining the sample and a compound to form a complex including the compound and the nucleic acid molecule; and detecting the nucleic acid molecule the complex including the compound and the nucleic acid molecule, thereby detecting the nucleic acid molecule, wherein the compound has the general formula (I):

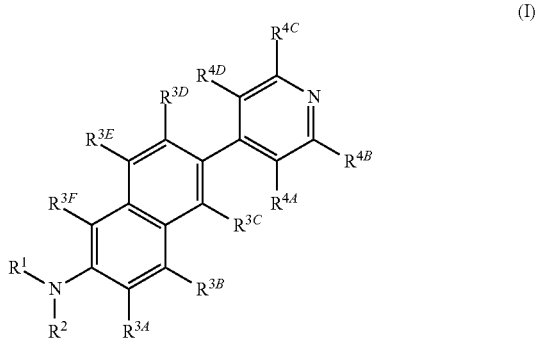

(I)

wherein each of R$^1$ and R$^2$ are independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein R$^1$ and R$^2$ are joined together to form a substituted or unsubstituted cycloalkyl, substituted or unsubstituted heterocycloalkyl, substituted or unsubstituted aryl, or substituted or unsubstituted heteroaryl; each of R$^{3A}$, R$^{3B}$, R$^{3C}$, R$^{3D}$, R$^{3E}$, R$^{3F}$, R$^{4A}$, R$^{4B}$, R$^{4C}$, and R$^{4D}$ are independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl; and salts and isomers thereof.

In yet another aspect, the present disclosure includes a method for detecting a nucleic acid molecule in a sample. The method can include combining the sample and a compound to form a complex including the compound and the nucleic acid molecule; and detecting the nucleic acid molecule the complex including the compound and the nucleic acid molecule, thereby detecting the nucleic acid molecule, wherein the compound has the general formula (II):

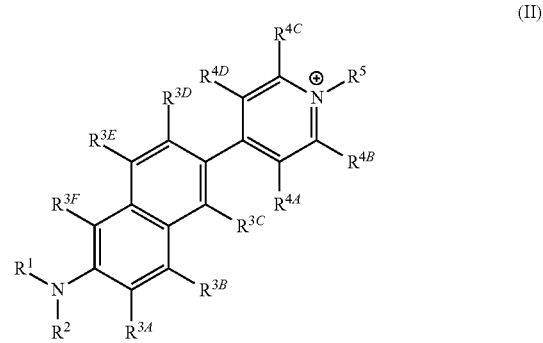

(II)

wherein each of R$^1$ and R$^2$ are independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein R$^1$ and R$^2$ are joined together to form a substituted or unsubstituted cycloalkyl, substituted or unsubstituted heterocycloalkyl, substituted or unsubstituted aryl, or substituted or unsubstituted heteroaryl; each of R$^{3A}$, R$^{3B}$, R$^{3C}$, R$^{3D}$, R$^{3E}$, R$^{3F}$, R$^{4A}$, R$^{4B}$, R$^{4C}$, and R$^{4D}$ are independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl; R$^5$ is selected from the group consisting of a halide, —CN, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl; and salts and isomers thereof.

In yet another aspect, the present disclosure further includes dielectric or semiconducting films including compounds of general formula (I) and/or general formula (II).

In yet another aspect, the present disclosure includes methods for detecting a nucleic acid molecule in a sample. The methods can include combining the sample and a compound to form a complex including the compound and the nucleic acid molecule; and defecting the nucleic acid molecule the complex including the compound and the nucleic acid molecule, thereby detecting the nucleic acid molecule, wherein the compound has the genera formula (I) and/or general formula (II).

In yet another aspect, the present disclosure includes methods of staining cells. The methods can include, e.g., combining a compound and the cell comprising a nucleic acid molecule to form a complex including the compound and the nucleic acid molecule, thereby staining the cell, wherein the compound has the genera formula (I) and/or general formula (II).

In yet another aspect, the present disclosure includes methods of determining a quantity of a nucleic acid molecule in a sample. The methods can include contacting the nucleic acid molecule in the sample with a compound to form a complex including the compound and the nucleic acid molecule; and determining the quantity of the nucleic acid molecule in the sample by at least measuring an amount of the compound complexed with the nucleic acid molecule, wherein the compound has the general formula (I) and/or general formula (II).

In yet another aspect, the present disclosure includes a compound having the general formula (III):

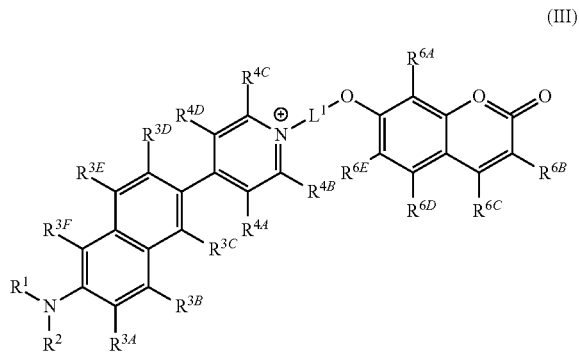

(III)

wherein each of $R^1$ and $R^2$ are independently selected from the group consisting of hydrogen, substituted or unsubstituted alkyl, substituted or unsubstituted heteroalkyl, substituted or unsubstituted acyl substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein $R^1$ and $R^2$ are joined together to form a substituted or unsubstituted cycloalkyl, substituted or unsubstituted heterocycloalkyl, substituted or unsubstituted aryl, or substituted or unsubstituted heteroaryl; each of $R^{3A}$, $R^{3B}$, $R^{3C}$, $R^{3D}$, $R^{3E}$, $R^{3F}$, $R^{4A}$, $R^{4B}$, $R^{4C}$, $R^{4D}$, $R^{6A}$, $R^{6B}$, $R^{6C}$, $R^{6D}$, and $R^{6E}$ are independently selected from the group consisting of hydrogen, a halide, —OH, —NH$_2$, —CN, —SH, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl; and $L^1$ is a linking group selected from the group consisting of substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene; and salts and isomers thereof.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows a binding titration curve of DNA with DANPY-1, in accordance with an embodiment of the present disclosure.

DETAILED DESCRIPTION OF THE INVENTION

The present disclosure provides compounds (e.g., fluorescent dyes) having affinity for nucleic acid molecules and/or having optical nonlinearity useful, e.g., for a variety of photonic applications. The present disclosure also provides surfactant-compound molecules that can be also, e.g., be used for various applications, such as photonic applications. The present disclosure further includes related methods of using the compounds.

As will be described further herein, the present disclosure is based at least in-part on the surprising discovery of new compounds that have high affinity for nucleic molecules (e.g., DNA) and/or can have optical nonlinearity useful for a variety of photonic applications. In some aspects, the present disclosure provides compounds that have an affinity for nucleic acid molecules and related methods of their use, such as detecting nucleic acid molecules (e.g., DNA), staining cells with fluorescent compounds, and/or determining a quantify of a nucleic acid molecule in a sample. In certain aspects, the present disclosure includes dielectric or semiconducting films including the compounds described further herein as well as related methods of making the films.

The term "nucleic acid" or "nucleic acid molecule" used herein may include DNA, RNA, natural or artificial polynucleotides and analogues and derivatives thereof. In some embodiments, the nucleic acid molecules can include deoxyribonucleic acid (DNA), double stranded DNA (dsDNA), cDNA, single stranded DNA (ssDNA), genomic DNA, mitochondrial DNA, cell-free DNA, ribonucleic acid (RNA), or transfer RNA (tRNA). The nucleic acid molecules can have a range of lengths, e.g., lengths sufficient to facilitate the binding affinity of the compounds described further herein. For example, nucleic acid molecules can have lengths between about 1-20 bases, between about 5-50 bases, between about 10-100 bases, between about 10-1000 bases, between about 10-10,000 bases, or between about 10-100,000 bases.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —(CH$_2$)$_n$, where n is 1, 2, 3, 4, 5 or 6. Alkylene groups include, but are not limited to, methylene, ethylene, propylene, isopropylene, butylene, isobutylene, sec-butylene, pentylene and hexylene.

The groups described herein can be substituted or unsubstituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can be a reactive group, such as but not limited to chloro, bromo, iodo, hydroxyl, or amino. Suitable substituents can be selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR'R"R'"Cl, —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —SO$_3$R', —SO$_3$Na, —SO$_3$K, —SO$_3$H, —PO$_3$Na$_2$, —PO$_3$H$_2$, —PO(OR')$_2$, —PO(OR')R", (—CN and —NO$_2$ in a number ranging from zero to (2m'+1), where m' is the total number of carbon atoms in such radical. R', R" and R'" each independently refer to hydrogen, unsubstituted (C$_1$-C$_8$)alkyl and heteroalkyl, unsubstituted aryl, alkoxy or thiolalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, per fluorinated. Halo-alkoxy includes, but is not limited to, trifluoromethoxy, 2,2,2,-trifluoroethoxy, perfluoroethoxy, etc.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C$_{3-8}$cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—.

As used herein, the term "heterocycloalkylene" refers to a heterocycloalkyl group, as defined above, linking at least two other groups. The two moieties linked to the heterocycloalkylene can be linked to the same atom or different atoms of the heterocycloalkylene.

As used herein, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy ($C_6H_5O$—). The present disclosure also includes alkoxy-heteroaryl or heteroaryloxy groups.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Suitable groups for the present disclosure can also include heteroarylene and heterarylene-oxy groups similar to the description above for arylene and arylene-oxy groups.

Similarly, aryl and heteroaryl groups described herein can be substituted or unsubstituted. Substituents for the aryl and heteroaryl groups are varied, such as alkyl, aryl, CN, amino, sulfide, aldehyde, ester, ether, acid, hydroxyl or halide. Substituents can be a reactive group, such as but not limited to chloro, bromo, iodo, hydroxyl, or amino. Substituents can be selected from: -halogen, —OR', —OC(O)R', —NR'R", —SR', —R', —CN, —NO$_2$, —CO$_2$R', —CONR'R", —C(O)R', —OC(O)NR'R", —NR'R"R'''Cl, —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —SO$_3$R', —SO$_3$Na, —SO$_3$K, —SO$_3$H, —PO$_3$Na$_2$, —PO$_3$H$_2$, —PO(OR')$_2$, —PO(OR')R", —N$_3$, —CH(Ph)$_2$, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl. The present disclosure also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkynyl-aryl include ethynyl-phenyl among others. The present disclosure also includes alkenyl-heteroaryl groups.

As used herein, the term "alkynyl-aryl" refers to a radical having both an alkynyl component and an aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present disclosure also includes alkynyl-heteroaryl groups.

In the present description, any concentration range, percentage range, ratio range, or integer range is to be understood to include the value of any integer within the recited range and, when appropriate, fractions thereof, unless otherwise indicated. As used herein, the term "about" means±20% the indicated value, range or structure, unless otherwise indicated.

As used herein and unless otherwise indicated, the terms "a" and "an" are taken to mean "one", "at least one" or "one or more". Unless otherwise required by context, singular terms used herein shall include pluralities and plural terms shall include the singular.

As described further herein, the present disclosure provides compounds having affinity for nucleic acid molecules and/or having optical nonlinearity useful, e.g., for a variety of electrooptic applications. In one aspect, the present disclosure includes fluorescent dye molecules that have an affinity for double stranded nucleic acid molecules (e.g., DNA). In some aspects, the fluorescent dye compounds can be used also for electrooptic applications and can be, e.g., incorporated into dielectric or semiconducting thin films. The compounds of the present disclosure can include, e.g., the variety of compounds described further herein. In some aspects, the compounds described herein can be referred to as DANPY dyes or DANPY compounds. The DANPY compounds can include a variety of analogues, derivatives and the like, and can include, e.g., the compounds disclosed in general formulas (I) and (II).

In some embodiments, the present disclosure includes a compound having the general formula (I):

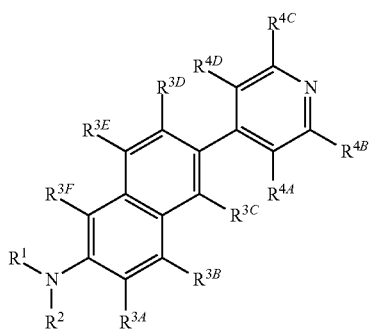

(I)

Each of $R^1$ and $R^2$ can be independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl. In some embodiments, $R^1$ and $R^2$ can be joined together to form a substituted or unsubstituted cycloalkyl, substituted or unsubstituted heterocycloalkyl, substituted or unsubstituted aryl, or substituted or unsubstituted heteroaryl. Each of $R^{3A}$, $R^{3B}$, $R^{3C}$, $R^{3D}$, $R^{3E}$, $R^{3F}$, $R^{4A}$, $R^{4B}$, $R^{4C}$, and $R^{4D}$ can be independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl. The present disclosure further includes salts and isomers thereof of the compounds in general formula (I).

As further described herein, the compounds (e.g., the DANPY compounds) can be cationic molecules (e.g., the compounds in general formula (II)). Some of the described syntheses of the cationic compounds can be made using an uncharged intermediate compound. Those uncharged intermediate compounds can include those described in general formula (I) above. Surprisingly, the generalized DANPY intermediate structure provides a base for fluorescent compounds of the present disclosure that have an affinity for nucleic acid molecules. For example, the uncharged intermediate for DANPY-1 (no functionalization at pyridine nitrogen) is a strong fluorophore and exhibits mild green fluorescence under ambient light. The strong fluorescence observed under more intense light sources could also be useful for imaging in less-polar environments than those accessible by the charged DANPY dyes. Another generalized structure for the intermediate, as well as an example of its intense fluorescence, is shown below. Other generalized structures of the intermediate are further described herein, e.g., in general formula (I).

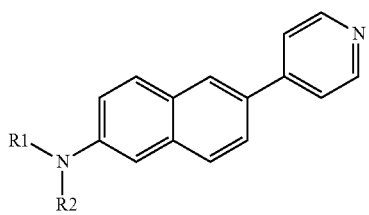

R1, R2 = alkyl, alkoxy, or aryl

As described herein, the present disclosure includes cationic compounds. In some embodiments, DANPY dyes can include a core tricyclic structure containing an aryl-aryl linkage between a functionalized naphthaleneamine and a functionalized pyridine. The naphthylaminopyridinium core can easily be functionalized at both the naphthaleneamine and pyridinium nitrogens. While methyl groups are added to all three sites for DANPY-1, alternative functionalization can be used to tune the position and width of absorbance and fluorescence peaks, as well as the molecular dipole moment and hyperpolarizability. Chain length can also be varied to tune solubility of the dye for use in different solvents, for selectively imaging different regions of cells, or for improving processibility for thin-film applications. As the dye can rely on donor-acceptor charge-transfer, the naphthaleneamine nitrogen can be substituted with electron-donating groups (e.g. alkyl chains), and the pyridinium nitrogen can be substituted with either electron-withdrawing groups (e.g. acyl groups) or alkyl chains. The following compound provides generalized structure of some example DANPY dyes:

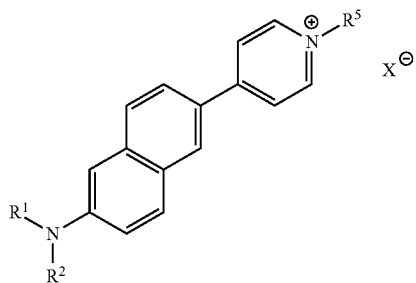

In some embodiments, $R^1$ and $R^2$ can be alkyl, alkoxy or aryl, $R^3$ can be alkyl aryl, acyl, perhaloalkyl, halide, or pseudohalide (e.g., cyano), and X can be an anion, including but not limited to halide, acetate, trifluoroacetate, or tosylate. $R^1$ and $R^2$ can also be part of the same cyclic system (e.g. a piperdine ring), and there is no need for the R-groups to be unique. In one example, in DANPY-1, $R^1$=$R^2$=$R^3$=methyl. In addition to the substitution at the nitrogens shown above, substitution of the aromatic system itself is also possible, including but not limited to addition of auxiliary electron-withdrawing or electron-donating groups, as well as groups to affect the sterics for the dye for biological binding and improved ordering electric field poling, vapor deposition, or crystal growth for the dye.

In some embodiments, the present disclosure includes a compound having the general formula (II):

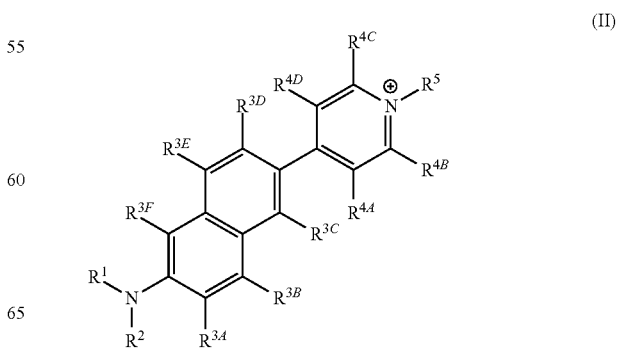

(II)

Each of R[1] and R[2] can be independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl. In some embodiments, R[1] and R[2] can be joined together to form a substituted or unsubstituted cycloalkyl, substituted or unsubstituted heterocycloalkyl, substituted or unsubstituted aryl, or substituted or unsubstituted heteroaryl.

Each of $R^{3A}$, $R^{3B}$, $R^{3C}$, $R^{3D}$, $R^{3E}$, $R^{3F}$, $R^{4A}$, $R^{4B}$, $R^{4C}$, and $R^{4D}$ can be independently selected from the group consisting of hydrogen, a halide, —OH, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl.

In certain embodiments, $R^5$ can be selected from the group consisting of a halide, —CN, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl. In some embodiments, $R^5$ can be selected from the group consisting of a halide, —CN, —NO$_2$, fluorinated alkyl, fluorinated heteroalkyl, fluorinated acyl, fluorinated alkoxy, fluorinated cycloalkyl, fluorinated heterocycloalkyl, fluorinated aryl, fluorinated heteroaryl, unsubstituted alkyl, unsubstituted heteroalkyl, unsubstituted acyl, unsubstituted alkoxy, unsubstituted cycloalkyl, unsubstituted heterocycloalkyl, unsubstituted aryl, and unsubstituted heteroaryl. The present disclosure further includes salts and isomers thereof of the compounds in general formula (II).

In some embodiments, the compounds of the present disclosure can have any one of the following formulas:

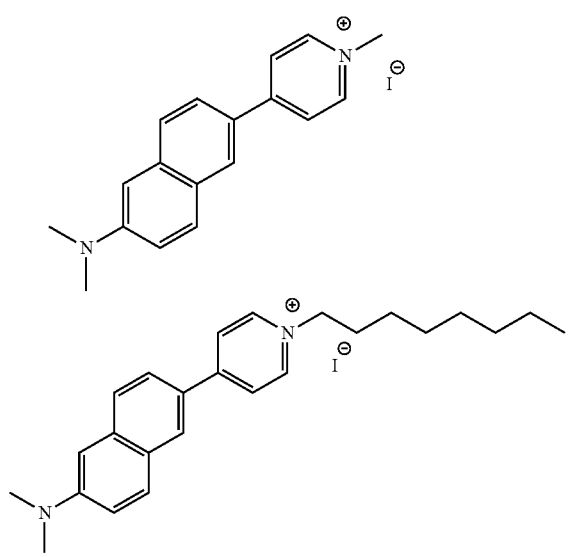

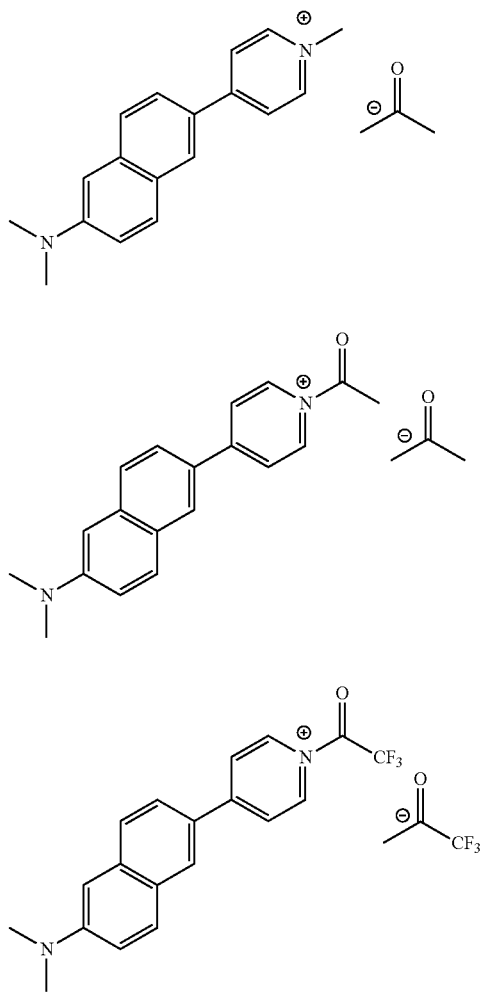

The DANPY compounds (e.g., compounds in general formula (I) and (II) can be made using a variety of techniques. Scheme 1 below shows an example method of making compounds of the present disclosure.

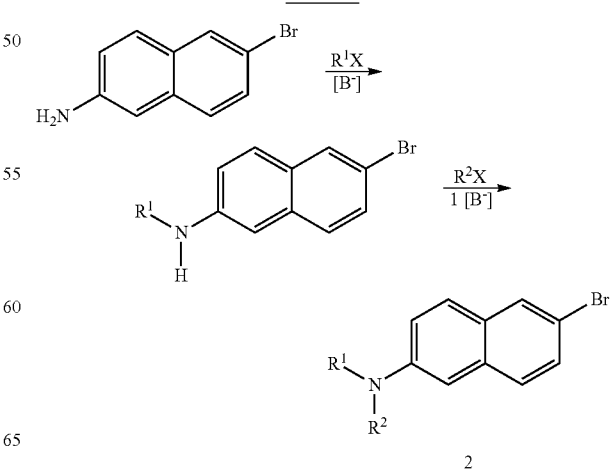

-continued

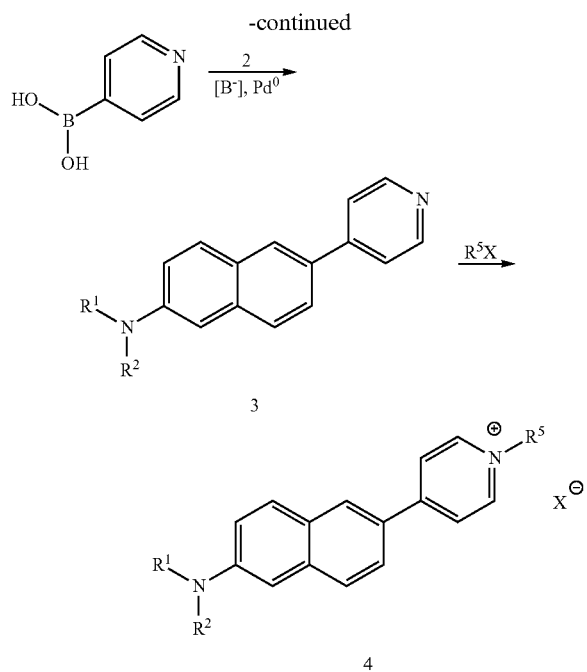

The example synthetic route in Scheme 1 can involve base-promoted alkylation of a commercially available naphthaleneamine such as 6-bromo-2-naphthaleneamine by alkylating agents of the form R—X, where X is a good leaving group (halide, tosylate, trifluoroacetate, etc.). If different substituents $R^1$ and $R^2$ are desired, purification of the mono-substituted product can be carried out before introducing the second substituent. If $R^1$ and $R^2$ are the same, one step can be carried out using a larger quantity of $R^1X$. Substitution on the naphthalene ring can be performed before or after alkylation. The alkylated naphthaleneamine can then be coupled to a substituted or unsubstituted pyridine derivative (e.g. to pyridine 4-boronic acid) using common aryl-aryl coupling reactions such as the Suzuki coupling. Finally, the purified compound with general formula (I) can be reacted with a substituted alkyl, aryl, or acyl compound of the form R—X at the pyridine nitrogen to form a pyridinium derivative with general formula (II). The nucleophilic substitution steps can be carried out in polar aprotic solvents, such as DMF or acetonitrile, and the coupling reaction can also be run in a polar solvent/solvent mixture such as 50:50 ethanol:acetonitrile.

In addition to the compounds described, e.g., in general formulas (I) and (II), the present disclosure further includes compound conjugates that can include e.g., a DANPY dye described herein conjugated to a coumarin dye by attachment, e.g., via a linking group. For example, the present disclosure can include conjugates having a generalized structure of DANPY compound-linking group-Coumarin dye. The DANPY compound can, e.g., include any of the compounds described herein such as those in general formula (I) and/or general formula (II). Linking groups can include any suitable group that can chemically link the DANPY compound to the coumarin dye. Coumarin dyes are known in the art and can further include derivatives and or analogues of coumarin-based dyes. The coumarin dyes can then be used to crosslink the coumarin conjugates. For example, coumarin dyes can photocrosslink under exposure to UV light. The photocrosslinking of the coumarin conjugates can be used for a variety of applications. As provided herein, e.g., the present disclosure includes dielectric or semiconducting films that can include, e.g., the coumarin conjugates. Depending on the concentrations of the coumarin conjugates in the film, strands of DNA with bound to fluorescent dyes herein can be anchored in the film and used, e.g., for electrooptic applications.

In some embodiments, the present disclosure includes a compound having the general formula (III):

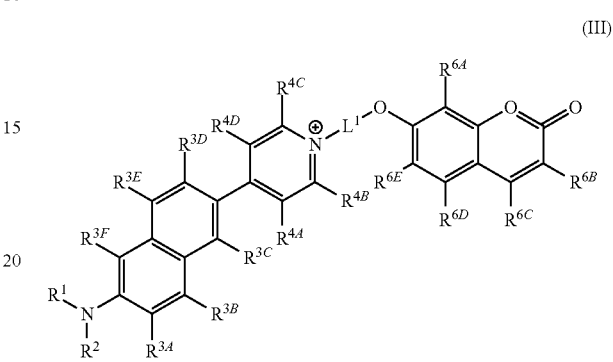

Each of $R^1$ and $R^2$ can be independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl. In some embodiments, $R^1$ and $R^2$ can be joined together to form a substituted or unsubstituted cycloalkyl, substituted or unsubstituted heterocycloalkyl, substituted or unsubstituted aryl, or substituted or unsubstituted heteroaryl.

Each of $R^{3A}$, $R^{3B}$, $R^{3C}$, $R^{3D}$, $R^{3E}$, $R^{3F}$, $R^{4A}$, $R^{4B}$, $R^{4C}$, $R^{4D}$, $R^{6A}$, $R^{6B}$, $R^{6C}$, $R^{6D}$, and $R^{6E}$ can be independently selected from the group consisting of hydrogen, a halide, —OH, —NH$_2$, —CN, —SH, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl.

$L^1$ can be a linking group selected from the group consisting of substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene. The present disclosure further includes salts and isomers thereof of the compounds in general formula (III).

As will be appreciated by one of ordinary skill in the art, the compounds of the present disclosure can be in the form of a salt (e.g., compounds in general formula (II)). For example, the compounds in general formula (II) can include a salt including a suitable couterion to the cationic compound. In some embodiments, the compounds of general formula (II) can include a salt including a counterion selected from the group consisting of a halide, a carboxylate (e.g., acetate, formate, and/or propionate), halogen-substituted carboxylate (e.g., halogen-substituted acetate), trifluoroacetate, and tosylate. In certain embodiments, the compounds of general formula (II) can include a salt having a counterion selected from the group consisting of I$^-$, O(C=O)CH$_3^-$, and O(C=O)CF$_3^-$.

The present disclosure further includes a wide variety of methods of using the compounds described further herein (e.g., the DANPY dyes). Owing in-part to their affinity for nucleic acids (e.g., DNA), the compounds of the present disclosure (e.g., compounds in general formula (I) and (II)) can be used generally for any use of dyes that having affinity for nucleic acid molecules that is generally well known in the art. For example, the compounds of the present disclosure can be used, e.g., for detecting nucleic acid molecules, quantifying nucleic acid molecules, and/or binding to nucleic acid molecules in cells and/or tissue. These methods of using fluorescent dyes having affinity for nucleic acid molecules (e.g., DNA) are generally well known in the art and can be applied with the compounds of the present disclosure described herein.

In some aspects, the present disclosure includes methods for detecting a nucleic acid molecule in a sample. For example, the present disclosure includes a method for detecting a nucleic acid molecule in a sample that can include combining the sample and a compound to form a complex including the compound and the nucleic acid molecule; and detecting the nucleic acid molecule, the complex including the compound and the nucleic acid molecule, thereby detecting the nucleic acid molecule. In certain embodiments, the compound has the general formula (I) or general formula (II), or any other compound described further herein as part of the present disclosure.

In certain aspects, the present disclosure includes methods of staining cells. For example, the present disclosure can include a method of staining a cell that includes combining a compound and the cell comprising a nucleic acid molecule to form a complex including the compound and the nucleic acid molecule, thereby staining the cell. In some embodiments, the compound has the genera formula (I) or the general formula (II), or any other compound described further herein as part of the present disclosure. In some embodiments, the methods of staining cells can include detecting the complex including the compound and the nucleic acid molecule.

In yet other aspects, the present disclosure includes methods for quantifying nucleic acid molecules in a sample. For example, the present disclosure can include a method of determining a quantity of a nucleic acid molecule in a sample that includes contacting the nucleic acid molecule in the sample with a compound to form a complex including the compound and the nucleic acid molecule; and determining the quantity of the nucleic acid molecule in the sample by at least measuring an amount of the compound complexed with the nucleic acid molecule. The compounds can have the genera formula (I) or the general formula (II), or any other compound described further herein as part of the present disclosure. As will be appreciated by one of ordinary skill in the art, a variety of methods can be used to facilitate quantification of a nucleic acid molecule in a sample. For example, calibration curves can be generated to provide accurate quantification of the nucleic acid molecules in the sample.

In some aspects, the present disclosure includes thin films including the compounds described further herein. For example, the present disclosure can include a dielectric or semiconducting film including a host material and a compound having the genera formula (I) or the general formula (II), or any other compound described further herein as part of the present disclosure. The films can be, for example, by combining the compound with the host material and forming the dielectric or semiconducting film on a substrate.

In yet another aspect, the present disclosure includes methods for quantifying nucleic acid molecules in a sample. For example, the present disclosure can include a method of determining a quantity of a nucleic acid molecule in a sample using the Quartz Crystal Microbalance with Dissipation Monitoring (QCM-D) method. QCM-D can be used to determine the formation of films (e.g., nm in thickness). For example, films may be formed on a surface from proteins, polymers, surfactants and cells. QCM-D can detect films formed in liquid and may be used to determine binding kinetics of, for example, cationic dyes (e.g., ethidium bromide, DANPY-1 and/or DAST). For example, a Q-Sense instrument (e.g., a Q-Sense E4 instrument, Biolin Scientific AB, Stockholm) can be used for QCM-D using a dedicated set of QCM sensors (e.g., $SiO_2$-coated). The procedures of cleaning, deposition, mass monitoring, and preparing nucleic acid for QCM-D are known. (R. J. Rawle, C. R. D. Selassie, M. S. Johal, *Langmuir* 2007, 23, 9563-9566). Data can be output as kinetics that can include structural changes and mass changes. The crystals can be, for example, coated with a polyethylene imine (PEI) layer to enable binding of anionic nucleic acids. The crystals can be, for example, coated with a polymer polystyrene sulfonate (PSS), that only undergoes loose electrostatic binding.

EXAMPLES

Example 1

Electro-optic devices based on organic materials typically use small-molecule dyes embedded within a host polymer, typically a common engineering polymer such as poly (methyl methacrylate) (PMMA) or amorphous polycarbonate (APC). However, biopolymers such as DNA can also be used as a host matrix when coated with surfactants such as CTMA (cetyl trimethylammonium chloride) or CTAB (cetyl triethylammonium bromide) to allow processing with common organic solvents. Such DNA-surfactant complexes possess several favorable properties, including an ordered local structure, low optical loss, and a tunable refractive index. They are also inexpensive to manufacture; as bulk DNA can be easily obtained from fisheries waste.

CTMA-DNA has also been used as a cladding layer in modulators developed with conventional guest-host organic glasses. (Grote, J. G. et al.; *J. Phys. Chem. B* 2004, 108 (25), 8585-8591.) Functioning electro-optic waveguide modulators have been demonstrated, using Disperse Red 1 (DR1) as the active dye. (Heckman, E. M. et al.; *App. Phys. Lett.* 2006, 89 (18), 181116). However, the electro-optic activity of previous all-biopolymer devices was much lower than state-of-the art devices based on organic glasses. The electro-optic coefficient, $r_{33}$, typically used to quantify EO performance, is given as:

$$r_{33} \propto \rho_N \beta_{zzz} \langle \cos^3 \theta \rangle \tag{1}$$

where $\rho_N$ is the number density of the active chromophores, $\beta_{zzz}$ is the molecular hyperpolarizability of the individual chromophores in the direction of the dipole moment, and $\langle \cos^3 \theta \rangle$ is the average acentric order of the chromophore dipole moments with respect to an applied field. All biopolymer-based EO devices have exhibited EO coefficients on the order of $r_{33}$=1-3, (pm/V), somewhat lower than DR1-based devices using conventional polymers. In comparison, monolithic organic glasses using high-$\beta$ chromophores have exhibited two orders of magnitude greater performance.

This discrepancy is likely due to the low intrinsic hyperpolarizability of DR1 compared to high-performance dyes such as CLD-1 and dye composites. Furthermore, DR1 does not bind well to DNA; it is possible that DR1 'semi-intercalates' in the surfactant layer. Pawlik, G. et al.; *Chem. Phys. Lett.* 2010, 484 (4-6), 321-323.) An ideal dye would have both a large hyperpolarizability and bind tightly to the DNA. This would allow exploitation of the ordered structure of DNA to enhance poling-induced acentric order (matrix-assisted poling).

This example describes a dye, DANPY-1 (dimethylaminonaphthylpyridinium), that draws inspiration from cationic organic nonlinear optical (ONLO) dyes such as DAST and from intercalating agents such as ethidium bromide to combine NLO activity with high affinity for DNA and the potential for future molecular engineering to improve performance. An example structure of DANPY-1 is shown as follows:

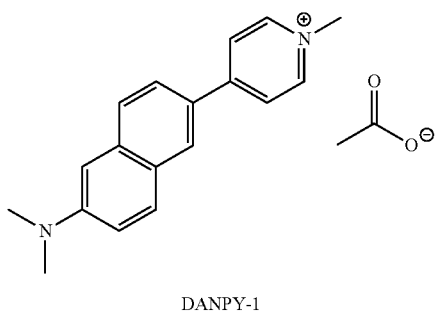

DANPY-1

After the dye, contained within the biomaterial, is poled, it can be hardened so that the poling-induced acentric order of the chromophores is preserved. Several crosslinking strategies have been proposed in which the DNA itself is crosslinked. As an example, PPIF (poly(phenyl isocyanate)-co-formaldehyde) has been used as a crosslinker in biopolymer films. To avoid chemical modification of the DNA on hardening, we have developed an alternative hardening procedure in which the surfactant, suitably modified, could act as a hardening agent. A goal was to combine the crosslinker and surfactant into a single compound, simplifying film processing and allowing fast crosslinking with ultraviolet light.

Coumarin was used as a photocrosslinkable moiety, as it undergoes a [2+2] cycloaddition upon exposure to UV light, connecting adjacent groups with a four-membered ring. At an appropriate mixing ratio with a conventional surfactant, such crosslinkable moieties could be used to anchor adjacent strands of DNA together, improving the material's resistance to both solvents and heat. The structure of our novel surfactant, Cou-C6 is compared to CTMA below:

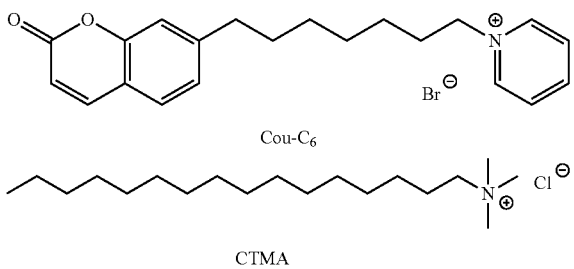

Cou-C6

CTMA

This example also includes methods for synthesis of materials. For example, the crosslinkable surfactant Cou-C$_6$ can be synthesized in two steps from commonly available starting materials. The synthesis is shown in Scheme 2:

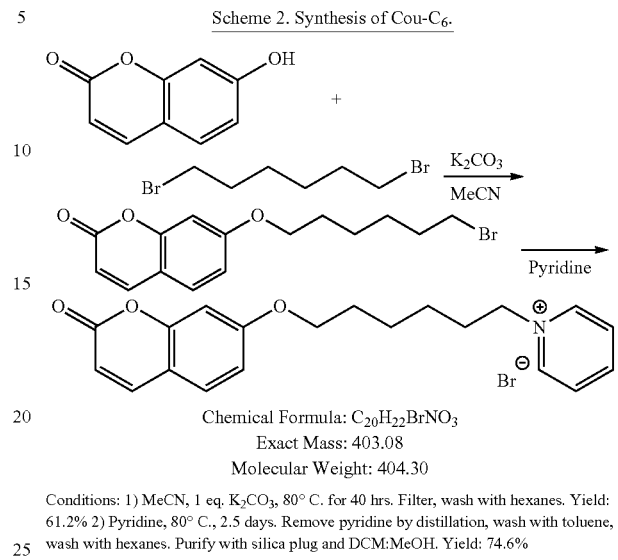

Scheme 2. Synthesis of Cou-C$_6$.

Chemical Formula: C$_{20}$H$_{22}$BrNO$_3$
Exact Mass: 403.08
Molecular Weight: 404.30

Conditions: 1) MeCN, 1 eq. K$_2$CO$_3$, 80° C. for 40 hrs. Filter, wash with hexanes. Yield: 61.2% 2) Pyridine, 80° C., 2.5 days. Remove pyridine by distillation, wash with toluene, wash with hexanes. Purify with silica plug and DCM:MeOH. Yield: 74.6%

Starting materials were purchased from Sigma Aldrich, Fisher Scientific, or J.T. Baker and used as received. All glassware was acid and base treated, and reactions were run under dry nitrogen. The identity of the product was confirmed by NMR (Bruker AV300) and ESI-MS (Bruker Esquire). The synthesis of the dye DANPY-1 is also short and straightforward, involving aryl-aryl coupling followed by methylation.

Example preparation of surfactant/DNA/crosslinker composites can be conducted in a variety of ways. Method 1 describes preparation of CTMA-Cou-DNA. The process of preparing crosslinkable CTMA-DNA is nearly identical to that of preparing CTAB-DNA or CTMA-DNA (Grote, J. G. et al.; *Proc. SPIE* 2003, 5211, 53-62, Heckman, E. M. et al., *Appl. Phys. Lett.* 2005, 87 (21), 211115), except that a fraction of the ordinary surfactant (e.g. CTMA) is replaced with the coumarin surfactant when preparing the initial aqueous solutions. The aqueous solution of the surfactants is then titrated into an aqueous solution of DNA, forming a white precipitate. This precipitate can be filtered off and can be re-suspended in short-chain alcohols such as methanol, ethanol or butanol. Water can be removed by filtration (though filter paper proved problematic) or centrifuging at ≥4500 RPM. If further purification is needed, the resulting solids can then be dissolved in ethanol, decanted or filtered using a coarse filter, and dried using rotary evaporation. The material will form a hard, transparent film on the inside of the flask used for evaporation.

Method 2 describes Addition to pre-coated DNA. The crosslinkable surfactant Cou-C$_6$ can also be added to existing CTMA-DNA or CTAB-DNA. Here, the CTMA-DNA, Cou-C$_6$, and any dyes used to prepare a film can dissolved in butanol directly before spin-coating, with the Cou-C$_6$ replacing a portion of the surfactant-coated DNA. Less Cou-C$_6$ should be used than with Method 1 due to limited solubility. Solutions can be used for spin-coating after mixing and heating. Unlike with Method 1, the DNA will not be stoichiometrically coated with surfactant, and free surfactant will remain in solution. Therefore, method 1 is preferred when possible.

Dye/DNA binding was assessed. The binding constant and number of dye molecules bound per base pair were assessed by means of photometric titrations (Peacocke, A. R.; Skerrett, J. N. H., *Trans. Faraday Soc.* 1956, 52, 261, Angerer, L. M.; Moudrianakis, E. N., *J. Mol. Bio.* 1972, 63, 505-521) of dye solutions with commercially available salmon sperm DNA (Sigma Aldrich, $M_W$ 50 kD to 100 kD) in 10 mM TE buffer at pH 7.2. Experiments were run using a temperature-controlled Ocean Optics diode array spectrophotometer at 25.0° C., with 2.5 mL of dye solution at a concentration sufficient for an initial optical density near 0.75, adding 1.5 mM DNA solution in 30 μL aliquots.

The nonlinear optical properties were characterized. The hyperpolarizability of DANPY-1 was determined using hyper-Rayleigh scattering (HRS) (Clays, K.; Persoons, A, *Rev. Sci. Ins.* 1992, 63 (6), 3285) in dichloromethane and methanol. Experiments were run using a femtosecond Ti:Sapphire laser at 800 nm, and fluorescence contributions to the signal were suppressed by means of fluorescence demodulation. Results were extrapolated to zero frequency using the two-level model. (Oudar, J. L.; Chemla, D. S., *J. Chem. Phys.* 1977, 66 (6), 2664-2668)

Crosslinking experiments were performed. Thin films of CTAB-DNA combined with Cou-$C_6$ prepared using Method 2, described above, and were spin-coated on glass slides from butanol. Two batches of films were made, one containing 15% Cou-$C_6$ by mass, and the other containing 30% Cou-$C_6$. Absorbance spectra of films were measured before and after crosslinking using a Varian Cary 5000 spectrophotometer. Films were crosslinked by exposure to broadband UV light from a 500 W mercury air lamp (Newport Optics) at a distance of 25 cm, using an exposure time of 5, 15, or 30 minutes. CTMA-Cou-DNA was also crosslinked in methanol solution following a similar protocol; spectra were measured al 25° C. Solution crosslinking experiments used an exposure time of 30 minutes.

Finally, the structure of DANPY-1 lends itself to further nationalization for compatibility with a DNA host. One possible modification is to add a coumarin-containing side chain similar to that used in $Cl^4$ in order to both avoid the need for a separate surfactant such as CTMA and allow for hardening of the film through photocrosslinking of the coumarins. (Tian et al., J. Polym. Sci. Part A: Polym. Chem. 2003, 41:2197-2206) A proposed synthesis for such a modified dye is shown in Scheme 3:

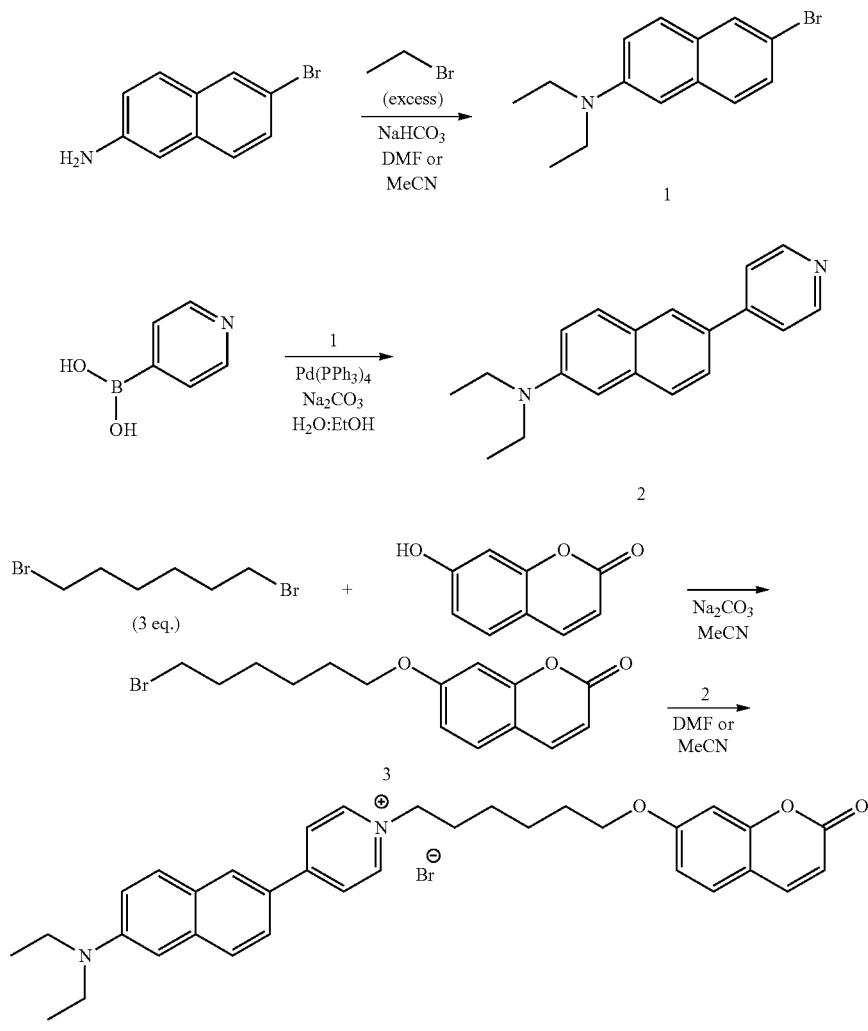

Scheme 3. Proposed synthesis of coumarin-functionalized LL-1 (or DANPY-1) variant A coumarin-based crosslinker based on structure (3) attached to pyridine has already been synthesized. 6-bromo-2-napthaleneamine was purchased from Astatech, and pyridine-4-boronic acid was purchased from Sigma-Aldrich, all other chemicals were purchased from Sigma Aldrich, Fisher Scientific, or Alfa Aesar. Commercially available chemicals, including solvents, were used as received. Solvents used for synthesis and chromatography were all of HPLC grade. Water used for making TE buffer was purified by reverse osmosis to a resistivity of >18 MΩcm$^{-1}$. Glassware was acid and base treated and oven dried before use. Synthetic procedures included the following:

(1) 6-bromo-2-napthaleneamine (1 eq), pyridine-4-boronic acid (1.1 eq), and sodium carbonate (3.7 eq) were added to a solution of 50% water and 50% ethanol in a double-necked round bottom flask. The solution was sparged with dry nitrogen for >30 min, then degassed by four cycles of exposing to vacuum and flushing with dry nitrogen. Tetrakis(triphenylphosphine)palladium(O) (0.01 eq) was added as a catalyst and the mixture was stirred overnight at 82° C. under dry nitrogen. Reaction progress was monitored by TLC and GC/MS. The mixture was then transferred to a separatory funnel, extracted with ethyl acetate, and washed with saturated aqueous NaHCO$_3$ and brine. The organic phase was retained, dried with anhydrous magnesium sulfate, and the solvent was removed in vacuo. The crude mixture was purified using silica gel chromatography eluting with 95% ethyl acetate and 5% methanol to afford a yellow powder (33% yield). C$_{15}$H$_{12}$N$_2$, m/z 221.2 (M+H, ESI), $^1$H NMR (500 MHz, CDCl$_3$) δ 8.66 (d, J=6.1 Hz, 1H), 7.99 (s, 1H), 7.75 (d, 8.5 Hz, 1H), 7.71-7.64 (m, 1H), 7.62 (d, J=6.1 Hz, 1H), 7.47 (s, 0H), 7.26 (d, J=0.6 Hz, 4H), 7.01 (s, 1H), 6.99 (d, J=2.1 Hz, 0H), 3.96 (s, 1H), 1.56 (s, 2H).

(2) Purified 1 was re-dissolved in DMF in a single-necked round bottom flask, and methyl iodide (5 eq) and sodium bicarbonate (1.9 eq) were added. The flask was sealed with a rubber septum and stirred at ambient temperature for 5 days. The reaction was monitored by TLC and ESI-MS, and an additional equivalent of methyl iodide was added on the final day to push the reaction toward completion. Upon completion, the mixture was filtered, washed with methanol, then degassed by rotary evaporation. The DMF was removed by distillation under vacuum (max temperature of 80° C.), and the crude product was dried in vacuo overnight, to yield an orange powder, C$_{18}$H$_{19}$N$_2$I, m/z 263.2 (M+, ESI)

(3) Crude 2 was purified using a silica gel plug with 90% dichloromethane and 10% methanol, acidified with glacial acetic acid to yield an orange product. The purified product was dried by rotary evaporation followed by 48 hours in vacuo at 90° C. to form a red powder. (55% yield) C$_{20}$H$_{22}$N$_2$O$_2$, m/z 263.15471 (M+, FAB). $^1$H NMR (300 MHz, MeOD) δ 8.74 (t, J=6.4 Hz, 2H), 8.42 (dd, J=15.4, 8.7 Hz, 3H), 7.94-7.74 (m, 3H), 7.32 (dd, J=9.2, 2.5 Hz, 1H), 7.00 (d, J=2.6 Hz, 1H), 6.78 (d, J=2.2 Hz, 0H), 4.89 (s, 8H), 4.34 (d, J=3.1 Hz, 3H), 3.33 (dt, J=3.3, 1.6 Hz, 10H), 3.15 (s, 4H), 2.94 (s, 1H), 2.7 (s, 2H), 1.94 (s, 5H), 1.39 (d, J=6.6 Hz, 1H).

Example 2

This example describes affinity of DANPY-1 to DNA. The affinity of DANPY-1 was compared to the common intercalating dye ethidium bromide by means of photometric titrations with DNA in aqueous buffer. The wavelength undergoing the largest absorption change (467 nm for ethidium bromide, 391 nm for DANPY-1) was used for determining the fraction of dye bound. An aqueous environment was chosen due to the observed lack of substantial binding between ethidium bromide and CTAB-DNA and concerns about difficulty in penetrating the tightly bound surfactant layer. These experiments were analyzed using the Scatchard equation (Scatchard, G., Ann. N.Y. Acad. Sci. 1949, 51, 662-672.)

$$\frac{r}{[DNA]} = nK - rK \tag{1}$$

where r is the ratio of bound dye to total DNA (bound or unbound), n is the number of binding sites occupied per base pair, and K is the binding constant. The concentration of DANPY used was substantially lower due to its higher extinction coefficient, and both runs only considered the region where [DNA]>[Dye]. DANPY-1 was found to have a 33% larger binding affinity than ethidium bromide. Furthermore, like ethidium bromide, it binds to only half of the sites (nearest-neighbor exclusion), providing evidence for possible intercalation. (Pohl, F. M.; Jovin, T. M.; Baehr, W.; Proc. Nat. Acad. Sci. 1972, 69 (2), 3805-3809, Cantor, C. R.; Schimmel, P. R., W. H. Freeman and Company: New York, 1980)

Dyes with high affinity for DNA can be cationic and contain multiple aromatic rings, while intercalators tend to have aromatic systems with low aspect ratios (nearly rectangular). Most dyes for EO applications, however, are uncharged and highly prolate in order to maximize the length of the π-system, and consequently, hyperpolarizability. Developing an ONLO dye capable of binding to DNA can include compromising between these characteristics. However, cationic ONLO dyes have been used to grow crystals for photonic applications, with the most successful of these dyes thus far being DAST (trans-4-[4-(Dimethylamino)styryl]-1-methylpyridinium toluenesulfonate). (Pan, F.; Wong, M, S.; Bosshard, C.; Günter, P., Adv. Mat. 1996, 8 (7), 592-595.) DAST has a structure analogous to DR1, but with a stilbene bridge instead of an azobenzene bridge, and a pyridinium acceptor instead of a nitro group. Both structures are shown in Scheme 2. However, as DAST is quite prolate, we sought to lower its aspect ratio and increase the size of its aromatic system, increasing its structural similarity to known intercalator ethidium bromide while maintaining its optical nonlinearity.

This example describes design of a structure based on the shape of ethidium bromide and DAST that would exhibit nonlinearity and bind to DNA. Candidate structures were examined by means of DFT calculations, including the structures shown below, comparing their hyperpolarizabilities and excitation energies to those of DAST.

a)

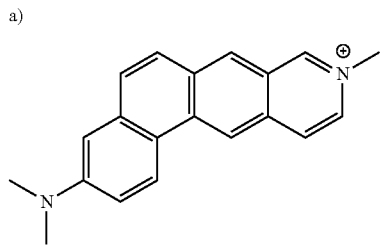

Chemical Formula: C$_{20}$H$_{19}$N$_2$$^+$
Molecular Weight: 287.38
Rel. B$_{zzz}$(B3LYP) = 1.15

-continued b)

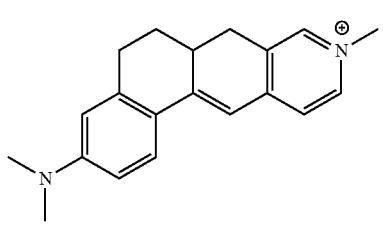

Chemical Formula: $C_{20}H_{23}N_2^+$
Molecular Weight: 291.41
Rel. $B_{zzz}$(B3LYP) = 0.87 c)

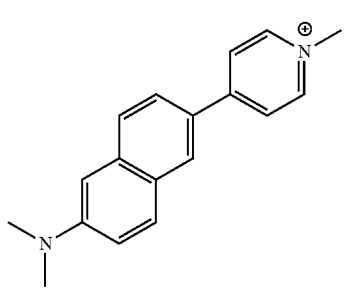

Chemical Formula: $C_{18}H_{19}N_2^+$
Molecular Weight: 263.36
Rel. $B_{zzz}$(B3LYP) = 1.33

Preliminary calculations were run at the B3LYP/6-31 G(d) level in vacuo using Gaussian '09, with hyperpolarizabilities calculated by analytic differentiation. Of the structures shown, structure c had the largest hyperpolarizability relative to DAST and could be synthesized from commercially available starting materials in few steps. It resembles the zwitterionic fluorescent dye BNBP (Ephardt, H.; Fromherz, P., *J. Phys. Chem.* 1993, 97 (17), 4540-4547), but without a captive anion and with shorter alkyl chains to reduce steric hinderance when approaching DNA.

The dye, DANPY-1 (internal name LL-1), can be synthesized by means of a Suzuki coupling (Leadbeater et al., Organic Process Research & Development 2006, 10 (4), 833-837; Zhang et al., *Synlett* 2005, (20), 3083-3086; Liu et al., Journal of Organic Chemistry 2005, 70 (15), 6122-5; Arvela, R. K.; Leadbeater, N. E., *Organic Letters* 2005, 7(11), 2101-2104)) to form (1), followed by methylation (Sommer et al., Journal of Organic Chemistry 1971, 36 (6), 824-828; Chiappe et al., Green Chemistry 2006, 8 (3), 277)) of both the pyridine and the aniline moieties to form an iodide salt (2). The iodide counter-ion can be replaced with a counter-ion of choice by varying the acid used in the purification of (3). Acetic acid was chosen for reasons of solvent compatibility, volatility, and convenience. The synthesis is shown in Scheme 4.

Scheme 4. Example synthesis of fluorescent dye LL-1 (or DANPY-1)

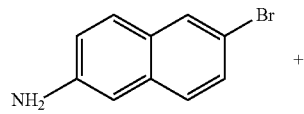
+

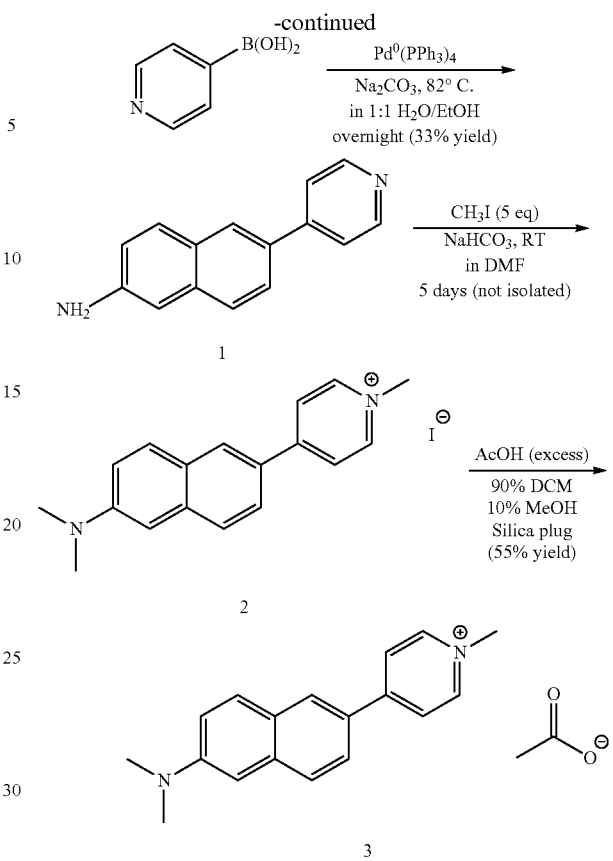

h steps in the synthesis are highly sensitive to the solvent used. In the methylation step, trimethylation occurred in DMF far more readily than in other polar, aprotic solvents. However, after five days, some dimethyl product remained, and an additional equivalent of methyl iodide was added on the final day to push the reaction toward completion. Instead of having the intended effect of converting remaining dimethylated 1 to 2, this resulted in formation of a blue-fluorescent baseline peak by TLC and corresponding appearance of a doubly ionized, tetramethylated peak (m/z=139.1) by mass spectrometry. As such, increasing the amount of methyl iodide used is not recommended for further synthetic pursuits.

Chromatographic separation of 3 proved difficult. Reasons for difficulty included low solubility in non-alcohol solvents, low mobility on normal phase silica gel, and close spacing in the elution of compounds differing by a single methyl group. However, a heavily acidified mixture of dichloromethane and methanol allowed for reasonable separation through a short column of normal phase silica gel. The high efficacy of the silica plug likely renders the other purification methods used for this step (filtration, solvent washes) redundant.

Experimental methods for this example include a general characterization methodology. UV/Vis spectra were recorded on a Varian Cary 5000 spectrophotometer using paired 1 cm fused quartz cuvettes and referenced against solvent. Fluorescence spectra were recorded on a Perkins-Elmer LS50B Luminescence Spectrophotometer using a 1 cm fused quartz fluorescence cuvette and an excitation wavelength of 400 nm. Circular dichroism spectra were recorded on a JASCO 720 Circular Dichroism Spectrophotometer using paired 100 mm fused quartz cuvettes and referenced against solvent. $^1$H NMR spectra were recorded on either a Bruker AV300 or AV301 spectrometer. Medium-resolution mass spectra were recorded on a Bruker Esquire ion trap mass spectrometer using electrospray ionization (ESI), and high-resolution mass spectra were recorded on a JEOL HX-110 double focusing mass spectrometer using fast atom bombardment (FAB) in a 3-nitrobenzyl alcohol matrix. Fluorescence images were recorded using Zeiss Fluorescent microscope with a BP 450-490 FT 510 LP 515 filter cube.

A titration methodology was also used. Dyes were evaluated for their DNA-binding properties by means of colorimetric titrations in buffered aqueous solution (1× TE buffer titrated to pH 7.2 with HCl). All titrations were run using an Ocean Optics diode-array UV/Vis spectrometer connected to a temperature control system. The thermal bath temperature was set to 25.0±0.1° C. (298 K). Initial dye solutions were typically 2.5 ml or 3.0 mL, with the concentration of the dye adjusted such that the optical density of the solution was between 0.60 and 0.90. DNA solution was added to the dye solution in 30 μL aliquots. Solutions were mixed by in-situ magnetic stirring, as well as manually shaking the cuvette after each addition. After allowing the solution to mix for about one minute, the stirrer was stopped and a spectrum was recorded. If the initial absorbance of the dye was ≥1, the dye solution was diluted with the appropriate solvent (TE buffer, methanol, or butanol) until the initial absorbance was <1. Runs continued until changes in absorbance became small (dilution only) or 450 μL of titrant was added, whichever was longer. Spectra were then examined to determine the wavelength at which the dye's absorbance changed most over the course of the titration. The reduced absorbance change $$Y = \frac{A - A_f}{A_b - A} \quad (2)$$

was calculated at the selected wavelength for each point in the titration. The absorbance of the free dye ($A_f$) was obtained from the initial absorbance value, and the absorbance of the bound dye ($A_b$) was obtained from linear regression of the absorbance values at the three highest measured concentrations of dye versus 1/[DNA]. This parameter was then used to calculate the fraction of dye bound, $$f_b = \frac{Y}{Y+1} \quad (3)$$

at each titrant concentration. Assuming an identical-and-independent-site binding model this fraction can also be written as $$f_b = \frac{[LN]}{[L] + [LN]} \quad (4)$$

where [L] is the concentration of unbound dye and [LN] is the concentration of bound dye. These can be determined from the equilibrium expression $$K = \frac{[LN]}{[L][N]} \quad (5)$$

and mass balance equations $$[L_0] = [L] + [LN] \quad (6)$$
$$[N_0] = [N] + [LN]$$

where [N] is the concentration of unbound DNA base pairs, [$L_0$] is the total concentration of dye, and [$N_0$] is the total concentration of dye. If it is further assumed that each dye has n sites (i.e. binding blocks access to adjacent sites), the fraction bound can be written in terms of two parameters, [$L_0$]$_i$ and [$N_0$]$_i$ for the ith measurement in a titration, and two variables, n and K:

$$f_{b,i} = \frac{1 + nK[L_0][N_0] - \sqrt{(-nk[L_0] - K[L_0] - 1)^2 - 4nK^2[L_0][N_0]}}{2nK[L_0]} \quad (7)$$

The resulting system of quadratic equations (one per point) can be solved by non-linear least-squares regression to find K and n. The fitting was done using an in-house, simulated-annealing based algorithm.

A Hyper-Rayleigh scattering methodology was used to characterize nonlinear optical activity. Hyper-Rayleigh scattering (HRS) measurements of the hyperpolarizability of LL-1 (or DANPY-1) were performed by Griet Depotter and Koen Clays at Katholieke Universiteit Leuven. Spectra were recorded in dichloromethane using a Ti:Sapphire laser with a fundamental wavelength of 800 nm, and referenced against Crystal Violet. Signal contamination from two-photon fluorescence was suppressed using high-frequency demodulation, and the hyperpolarizability was extrapolated to zero frequency using the two-level model, with component along the chromophore dipole assumed to be the dominant tensor element.

Absorbance and fluorescence spectra of LL-1 (or DANPY-1) were recorded in four solvents (TE buffer at pH 7.2, methanol, dimethyl sulfoxide, and chloroform). Obtaining quantitative extinction coefficients required sample preparation to be carried out in a glovebox under dry nitrogen, as the dye was very hygroscopic. However, the extinction coefficients obtained compare favorably to that of ethidium bromide (5800±200 M$^{-1}$ cm$^{-1}$ at 480 nm in aqueous solution) (Pohl, F. M. et al.; *Proc. Nat. Acad. Sci.* 1972, 69 (12), 3805-3809) and are consistent with dyes with similar structures to LL-1 (or DANPY-1). Absorbance and emission maxima are listed in Table 1.

TABLE 1

Linear optical properties of DANPY-1

| Solvent | ε (dielectric) | $\lambda_{max}$ (abs, nm) | $\epsilon_{max}$ (M$^{-1}$ cm$^{-1}$) | $\lambda_{max}$ (fluor, nm) |
|---|---|---|---|---|
| TE buffer | 80.1 (water) | 409 | 17000 | 611 |
| Methanol | 33.0 | 445 | 20000 | 604 |
| DMSO | 47.24 | 442 | qualitative | 614 |
| Chloroform | 4.8064 | 468 | qualitative | 556 |

LL-1 (or DANPY-1) exhibits strong negative solvatochromism in its absorbance maximum, with a hypsochromic shift of 59 nm between chloroform and water. However, it shows positive solvatochromism in its fluorescence maximum. These shifts are consistent with those observed for similar hemicyanine dyes with aryl-aryl linkages. Fromherz explains this symmetrical solvatochromism by reversal of the molecular dipole moment between the ground and exerted states. (Fromherz, P., *J. Phys. Chem.* 1995, 99 (18), 7188-9192) The dye exhibits a large Stokes shift in all solvents, peaking at 202 nm in TE buffer, although it is substantially reduced in less polar solvents by the symmetrical solvatochromism. (Spectra data is not shown.)

The shape of the absorbance spectra is similar in all four solvents, with a single broad peak in the visible and a shoulder leading into a peak in the ultraviolet. The fluorescence spectra all exhibit a single broad peak, with the exception of the measurement in TE buffer, which shows a shoulder at about 500 nm and about half the intensity of the primary peak. As the solution in TE buffer is the only one containing substantial concentrations of other ionic species, this peak could be due to complexation with the Tris or EDTA in the buffer.

Nonlinear optical properties were analyzed. The hyperpolarizability of LL-1 (or DANPY-1) was investigated computationally, as well as experimentally by Hyper-Rayleigh scattering. As the B3LYP functional used for preliminary screening of molecular hyperpolarizabilities is known to overestimate charge transfer over long distances, additional electronic structure calculations were run using the heavily parameterized M062X functional, which has previously shown good performance for calculating relative hyperpolarizabilities, as well as with ab initio second-order Møller-Plesset Perturbation Theory (MP2). All calculations were run with Gaussian 09, and hyperpolarizabilities were obtained by numerical (finite-field) differentiation of polarizabilities that were calculated by analytic differentiation. Results are listed in Table 2.

TABLE 2

Static hyperpolarizability along the molecular dipole axis ($\beta_{zzz}$, $10^{-30}$ esu, perturbation convention) of LL-1 in different dielectric environments.

| Method | Vacuum | Chloroform | Methanol |
|---|---|---|---|
| B3LYP/6-31 + g(d) | −107 | −184 | −290 |
| M062X/6-31 + g(d) | −111 | −157 | −151 |
| MP2/6-31 + g(d)/MP2/6-31g(d) | −128 | −104 | −86 |

In all cases, DANPY-1 exhibits a negative $\beta_{zzz}$, a characteristic typically seen in zwitterionic chromophores, which indicates that charge transfer occurs in the direction opposite the molecular dipole moment. The magnitude of the static hyperpolarizability ($\beta_{zzz}(0)$) compares favorably in all three solvent environments with that of DR1 ($54\pm5\times10^{-30}$ esu in chloroform, extrapolated to zero frequency). Interestingly, while both DFT methods predict that hyperpolarizability will increase with solvent polarity, consistent with most neutral ground state ONLO chromophores, the MP2 calculations predict that the hyperpolarizability will decrease as solvent polarity is increased. Experimental HRS data closely resembled the MP2 predicted value, with an extrapolated $\beta_{zzz}(0)$ of $90\pm3$ in dichloromethane. As HRS measurements are derived from a rotational average, the sign of beta cannot be determined. Follow-up calculations at the MP2/6-31+g (d) level in dichloromethane obtained a $\beta_{zzz}(0)$ of −95; calculations with a larger (aug-cc-pVDZ) basis set obtained a slightly larger $\beta_{zzz}(0)$ of −114. Additionally, the hyperpolarizability is comparable to measurements of DAST variant MO by Clays and co-workers ($140\pm10\times10^{-30}$ esu in chloroform, extrapolated to zero frequency), providing further evidence for similar optical nonlinearity between DANPY-1 and DAST. (Olbrechts, G. et al.; *Opt. Lett.* 1999, 24 (6), 403-405.)

Binding titrations were run for DANPY-1 (or LL-1), DAST, and ethidium bromide as a control, (data not shown) All three exhibited a shift in absorbance maximum upon addition of DNA and show a single isosbestic point in the visible region of the spectrum, supporting the use of the two-species (bound and unbound) model. As DR1 is not sufficiently soluble in water, an exact comparison with the other three dyes was not possible, but a titration in 1:1 TE buffer and ethanol showed no substantial change in the absorbance peak. The magnitude of the change in wavelength as DNA is added is far greater for LL-1 and ethidium bromide. Data for both of these dyes was fit using equations to produce binding curves. The control run for ethidium bromide produced data reasonably consistent with prior experiments, with n=1.91±0.015, compared to 2.17 (using our convention of base pairs/dye) at 20° C. in a CsCl/EDTA solution. (Tinoco, I.; Sauer, K.; Wang, J. C.; Puglisi, J. D., *Physical Chemistry: Principles and Applications in Biological Sciences,* 4th ed.: Prentice-Hall: Upper Saddle River, N.J., 2002.) The n=2 binding model for DNA is often indicative of intercalation, as an intercalated dye molecule is inserted between two base pairs, distorting the shape of the DNA helix. Binding curves for LL-1 (see, e.g., FIG. 1) were also fit best by the n=2 model, although the slope of the n-K error surface was shallow near the minimum. Combined with the large red shift (indicative of a lower dielectric environment), these data illustrate that LL-1 likely intercalates into DNA.

However, as the binding curves only indicate the number of base pairs needed to bind one dye molecule, without suggesting any particular ordering of the dye molecules, the electronic circular dichroism in the UV of both LL-1 and ethidium bromide was measured. In circular dichroism measurements, unperturbed DNA exhibits a positive peak about 275 nm and a negative peak about 245 nm. When ethidium bromide is added to the DNA solution, the peak is not only distorted, but an additional peak appears in a wavelength range corresponding to the UV absorbance of ethidium bromide. No such peak is observed for LL-1, although this does not rule out intercalation; steric characteristics may cause the difference in results between ethidium bromide and LL-1. Unlike LL-1, ethidium bromide has a bulky phenyl group projecting out from the plane of the main aromatic system. Thus, this side group may bias the direction in which ethidium intercalates and enhance its response to circularly polarized light. Circular dichroism spectra not shown.

Example 3

In addition to the in vitro experiments mentioned above, LL-1 (or DANPY-1) was also evaluated in living cells as a stain for fluorescence microscopy applications. When dissolved in DMSO, it proved capable of crossing the cell membrane of *Gymnodinium* sp and accumulating in the nucleus, where it fluoresced yellow when excited by light in the 450-490 nm range, (data not shown.

In another aspect, this example describes a set of experiments to investigate DANPY-1 dye for use in flow cytometric analysts of DNA. The alga Prorocentrum minimum was selected for these studies. Several controls were run to: (a) ensure that cell integrity was maintained, (b) assess the contribution of unbound DANPY-1 to fluorescent background signals and (c) determine a dye concentration and the intensity of the fluorescent signal when the target DNA is fully saturated with bound dye. The DANPY-1 concentrations that were tested in these preliminary experiments ranged from 7.1 µM to 228 µM. All of the flow cytometric work was performed on an Accuri C6 flow cytometer (BD Scientific, Ann Arbor, Mich.). The excitation wavelength for the FL1, FL2, and FL3 detectors (or channels) is 488 nm and the FL4 laser excites at a wavelength of 640 nm. The fluorescent wavelengths that each channel detects are as follows: FL1 530/30, FL2 585/40, FL3 670 LP and FL4 675/25. These experiments are summarized below (data not shown):

(1) Procentrum minimum with no DMSO and no DANPY-1: The Procentrum minimum cell density is 1.16e5 cells/mL based on the P2 gate of data from well A01 after a 2-min count. The events in the P2 gate correlates to the chlorophyll fluorescent signature of Prorocentrum minimum cells. Results reflected a cell density of 9.4e4 cells/mL after a 10-minute count.

(2) Procentrum minimum with 1% DMSO added but no DANPY-1 Dye added: The measured cell concentration in well A03 was 1.02e5 cells/mL, which was similar to the non-DMSO control measured in A02. This data indicates that no impact on cell integrity occurs when cells are exposed to 1% DMSO. The FL1 and FL2 graphs from sample A03 have fluorescence signal 1788 and 3121 respectively when no DANPY-1 is added to the cells.

(3A) Prorocentrum minimum with 1% DMSO and 7.1 µM DANPY-1 dye added and (3B) No cells with 1% DMSO and 7.1 µM DANPY-1 dye added: The cell concentration in well A04 was 1.02e5 cells/mL, which was similar to the non DMSO control well A02, indicating there was no impact on cell integrity after exposure to 1% DMSO in the presence of 7.1 µM DANPY-1 dye during a 10 minute exposure. Results in plots of FL1 and FL2 show that the cells are not fully saturated at 7.1 µM as indicated by the continued rise in the intensity of events over the 10 minute time course of the experiment. The mean fluorescent intensity for the FL-1 and FL-2 channels was 6032 and 40801, respectively. Two-minute time course plot of FL1 and FL2, shown in well C04 the non-cell DANPY-1 control, show the fluorescent signal of 217 and 858, respectively, when not bound to DNA.

(4A) Prorocentrum minimum with 1% DMSO and 57 µM DANPY-1 dye added and (4B) No cells with 1% DMSO and 57 µM DANPY-1 dye added: The cell concentration in well A05 was 9.5e4 cells/mL, similar to the non DMSO control well A02, indicating there was no impact on cell integrity from the presence of 1% DMSO or 57 µM DANPY-1 dye during a 10 minute exposure. The 10-minute time course plots of FL1 and FL2 show that the cells are not fully saturated at 57 µM because the fluorescent intensity of the events continues to rise over 10 minute. The mean FU intensity for the FL-1 and FL-2 channels was 17951 and 167481, respectively. Two minute time course plots of FL1 and FL2 show the fluorescent signal of 194 and 582, respectively, when not bound to DNA.

(5A) Prorocentrum minimum with 1% DMSO and 228 µM DANPY-1 dye added and (5B) No cells with 1% DMSO and 228 µM DANPY-1 dye added: The cell concentration in well A06 was 8.1e4 cells/mL, slightly lower than that observed for the non-DMSO, non DANPY-1 control in well A02, indicating that some impact on cell integrity from the 1% DMSO and/or DANPY-1 at 228 µM during 10 min of exposure has occurred. The 10-minute time course plots of FL1 and FL2 show that the cells are saturated at 228 µM. The fluorescent intensity of the events remains constant over the 10-minute assay period. The mean, fluorescent intensity for the FL-1 and FL-2 channels was 26131 and 412988, respectively. The 2-minute time course plots of FL1 and FL2, shown in well C06 the non-cell DANPY-1 control, show the fluorescent signal of 237 and 1084, respectively, when not bound to DNA.

The results indicate DANPY-1 is successfully penetrating Prorocentrum minimum while maintaining cellular integrity. At 7.1 and 57 µM the dye does not fully saturate the available DNA binding sites within 10 minutes, suggesting that a longer incubation is necessary for this organism. The FL-2 channel on the flow cytometer shows a much higher response than FL-1, indicating it may be possible to use dye concentrations below 7.1 µM, increase exposure time and still obtain an excellent fluorescent signal. Lower dye concentrations are desirable because the probably of cell viability increases, nonspecific staining is greatly diminished and only minute amounts of dye are used. The non-cell controls containing DANPY-1 also reveal a large difference between background signal and bound stain aiding in clearly delineating stained cells. It should be noted that Prorocentrum minimum is an alga that has a DNA content that is unusually large—greater than that of all prokaryotic and almost all eukaryotic taxa (500-2000×). It is likely that cells having smaller genomes will be easily stained using this dye.

Example 4

This example describes synthetic efforts related to DANPY-1 and other variants that, e.g., have modified hyperpolarizability and can have increased synthetic yields of steps in the synthesis. For example, in some aspects, improvement in synthetic efficiency can be obtained by alkylating the bromonaphthalenamine before the Suzuki coupling; this allows far easier removal of the DMF and separation of the uncharged Suzuki product. The final methylation can then be run in lower-boiling acetonitrile, simplifying drying of the dye. The uncharged intermediate can also be used to add alternate acceptors or vary the length of the alkyl chain.

An example synthesis of a DANPY intermediate is shown below:

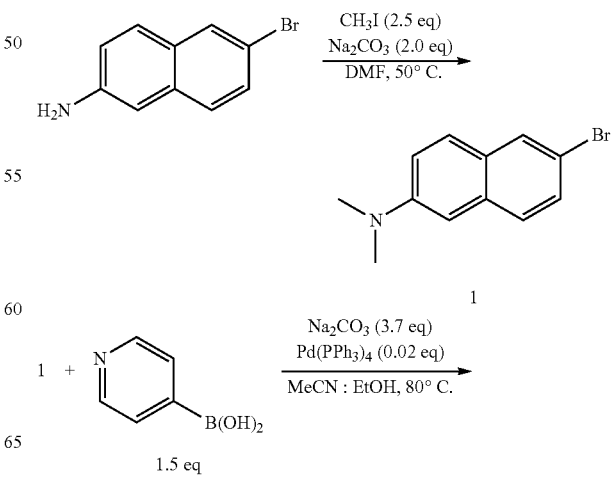

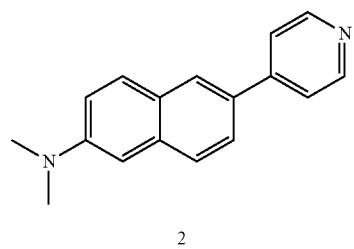

2

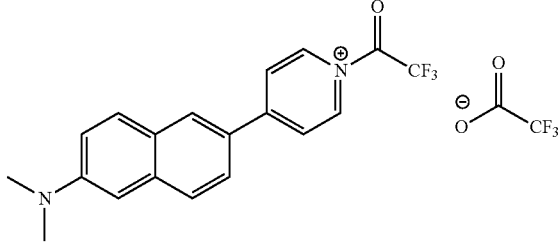

6

Yields for the first step have been in the 60-80% range; the second step yielded approximately 50%. Very little impurities were seen in GC/MS of crude 2, indicating that the low yield may be due loss of a large quantity of product in the H2O:EtOAc extraction. The final product could be readily recrystallized from water and ethanol.

Intermediate 2 was used to make three additional variants of the dye (4-6). The syntheses of all three of these variants, as well as the DANPY-1 core before ion exchange (3), are shown as follows:

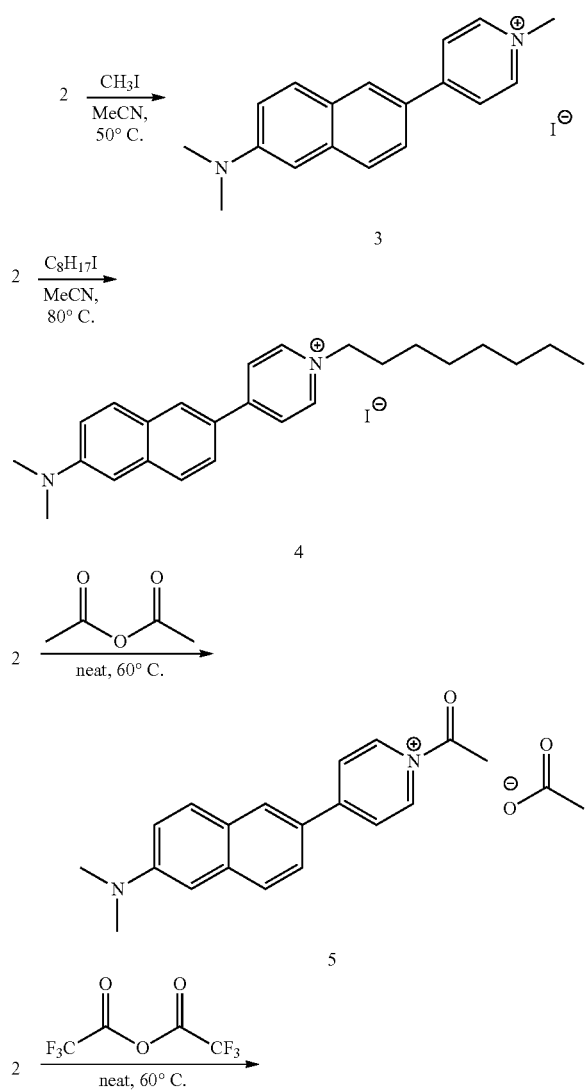

DANPY-1 can be produced by running 3 through a silica plug (90% DCM, 9% MeOH, 1% glacial acetic acid), which exchanges the iodide counterion for an acetate counterion. The same procedure can be performed with 4, with the product known as DANPY-$C_8$. This dye has been produced in purified form in small quantities and is being characterized for biological imaging, but its binding to DNA has not yet been quantified in vitro.

Synthetic Details: Intermediate 1:

987 mg 6-bromo-2-naphthaleneamine, 953 mg $Na_2CO_3$ (2 eq), 700 μL MeI, in 80 mL of DMF were added to a round bottom flask. The reaction was run at 50° C. for 25.5 hours. DMF was removed by extraction with ethyl acetate and 3× $H_2O$+1× brine. Dried with $MgSO_4$. Majority product was dimethyl by GC/MS. Product was purified on a silica gel column with 67% hexanes and 33% ethyl acetate. Obtained 640 mg of product (58% yield).

Intermediate 2:

640 mg of LEJ-2-108, 432 mg of pyridine-4-boronic acid (1.36 eq), 1006 mg $Na_2CO_3$ (3.7 eq), and 62 mg $Pd(PPh_3)_4$ (0.02 eq) were added to 80 mL of degassed 1:1 MeCN:EtOH in a round bottom flask. The reaction mixture was refluxed (~80° C.) overnight under dry nitrogen. The solvent was removed by rotary evaporation, with the solids resuspended in ethyl acetate and extracted 2× with H2O, 1× with brine. The product was recrystallized from hot H2O:EtOAc, obtaining 300 mg of purified 2. (47% yield).

Product 4:

44 mg of intermediate 2 and 6 mL acetic anhydride (neat) were added to a round bottom flask. The reaction was run at 60° C. for 24 hours under dry nitrogen. Trace product was detected by ESI-MS and TLC but not isolated.

Product 5:

140 mg of intermediate 2 and 16 mL trifluoroacetic anhydride were combined in a round bottom flask. The reaction was run at reflux for 24 hours under dry nitrogen. TFAA was removed in vacuo and 62 mg crude product was obtained. Recrystalization from Toluene:MeCN gave negligible yield. Product was present by ESI-MS and NMR but not isolated in substantial quantities.

Product 6:

50 mg of intermediate 2, 40 μL iodooctane (1.5 eq) and 10 mL of MeCN were added to a round bottom flask. The reaction was run for 48 hours at 85° C. (reflux) under dry nitrogen. The product was purified on a silica gel column with 90% DCM, 9% MeOH, 1% acetic acid, 76 mg of semi-pure product (89% crude yield) were obtained from the column. This product was recrystallized from hot Toluene: EtOH, isolating 3 mg (3.5% final yield) due to poor recrystallization efficiency, although semi-pure residual product from the recrystallization was retained as well.

Another variant includes DANPY-TFA (trifluoroacetic acid) with cyano groups ortho to the pyridinium nitrogen and an arylamine donor (CAM-B3LYP $\beta_{zzz}$=681, as shown below:

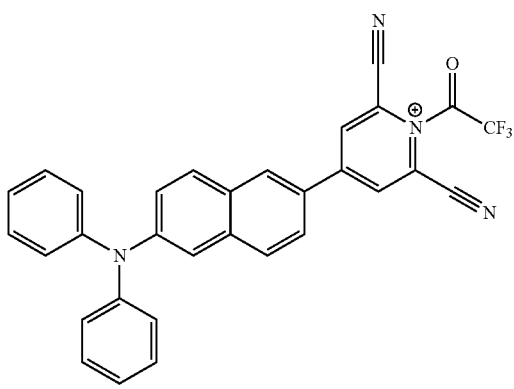

Chemical Formula: $C_{31}H_{16}F_3N_4O^+$
Molecular Weight: 519.50

The synthetic experiments conducted thus far have indicated that both the hyperpolarizability and hydrophobicity of the DANPY core can be tuned by altering the substitution at the two nitrogens, allowing for development of DANPY-based dyes the could be used to directly coat DNA, and if responsive to poling, would provide enhanced electro-optic activity.

Example 5

This example describes making of thin films with DANPY dyes. DANPY can be poorly soluble in standard spin-coating solvents such as TCE and cyclopentanone. It can also be poorly soluble in butanol, which is typically used for spin-coating CTMA-DNA solutions. It is, however, highly soluble in lower alcohols such as methanol, ethanol, and n-propanol. However, common NLO host materials such as PMMA and APC are poorly soluble in these solvents. As a preliminary test before further work attempting to incorporate the dye into CTMA-DNA, a series of poling experiments was run using DANPY in ethanol, using two alcohol-soluble polymers, poly-(4-vinylpyridine) (P4VP) and poly-(4-vinylphenol) (PVP) as host materials.

Concentrations ranging from 10% DANPY to 25%, DANPY were examined; the maximum soluble concentration of DANPY in ethanol at 20° C. is somewhere between 10% and 12%. Solutions were prepared on a small scale, with approximately 0.5 mL of liquid per solution. After preparation, solutions were agitated on a roller overnight, heated to ~50° C., and allowed to cool back to RT on the roller before use. A solution volume of 50 μL was used for all batches except for LEJ-2-152, which used a volume of 40 μL. Spin coating conditions are detailed in Table 3.

TABLE 3

Spin-coating conditions and thicknesses

| Batch | Polymer | Solids % | Dye % | Spin Protocol | Thickness (μm) |
|---|---|---|---|---|---|
| 1 | P4VP | 10 | 10 | A | 1.0 to 1.9 |
| 2 | P4VP | 6 | 25 | B | 0.5 to 0.8 |
| 3 | P4VP | 6.25 | 12 | B | 0.4 to 0.6 |
| 4 | PVP | 7.5 | 14 | C | 0.4 to 0.7 |
| 5 | PVP | 7.5 | 14 | B | ~0.4 |
| 6 | PVP | 10 | 10 | D | 0.4 to 0.6 |
| 7 | PVP | 10 | 10 | E | ~0.7 |

Note:
Batches 4 and 5 were batches made using different spinning protocols from a single solution, as were batches 6 and 7.

The spin protocols were as follows: A. 40 s at 450 RPM, 50 s at 850 RPM, 15 s at 2000 RPM, unfiltered, spun at RT; B. 5 s at 450 RPM, 50 s at 850 RPM, 15 s at 2000 RPM, unfiltered, spun at RT; C. 5 s at 450 RPM, 50 s at 850 RPM, 15 s at 2000 RPM, unaltered, spun at 65° C.; D. 5 s at 500 RPM, 30 s at 800 RPM, 15 s at 1500 RPM, filtered (0.2 μm PTFE), spun at RT; E, 15 s at 500 RPM, 30 s at 700 RPM, 15 s at 1500 RPM, filtered (0.2 μm PTFE), spun at RT.

Absorption spectra of the films indicated that the linear optical properties of the dye were changed little from chloroform solution, (data not shown) The optical density of the films was also quite low compared to typical EO films, with an optical density of only 0.35 for a film a 1.0 μm film at 10% chromophore loading.

Example 6

This example describes use of Quartz Crystal Microbalance with Dissipation Monitoring (QCM-D) to determine binding of dyes (e.g., cationic) to different types of nucleic acids. Data comprising the results of a QCM-D analysis using three cationic dyes; (1) ethidium bromide, a DNA intercalator, (2) DANPY-1, a nucleic acid stain, and (3) DAST, a commercial dye intended for nonlinear optics applications are described below and results presented in table 4. Of note, DAST lacks the planar aromatic system of ethidium bromide and DANPY-1 and may bind nucleic acids by simple ion pairing Experiments were performed using a Q-Sense E4 instrument (Biolin Scientific AB, Stockholm) with a dedicated set of $SiO_2$-coated QCM sensors. The method was run under continuous flow conditions at a flow rate of 0.3 mL/min and a temperature of 298 K. The cleaning, deposition, mass monitoring, and single-stranded DNA preparation procedures are commonly used by those skilled in the art. The DNA used was commercially prepared salmon testes Na-DNA, and all other chemicals, were purchased from Sigma-Aldrich and used as received. Polymers were adsorbed onto the QCM crystals in situ from pH 7.2 1× TE buffer. Nucleic acid solutions were 1.5 mM and dye solutions ranged from 0.3 to 0.5 mM.

The three nucleic acids (e.g., single-stranded DNA (ssDNA), double-stranded DNA (dsDNA), and transfer RNA (tRNA)) used in this example are anionic. The crystals were coated with a polyethylene imine (PEI) layer to create a surface and enable binding of the nucleic acids. The ethidium bromide, DANPY-1 and DAST nucleic acid dyes did not bind to the PEI layer. Polystyrene sulfonate (PSS) was used as a control polymer. As controls, PSS which can only undergo loose electrostatic binding, and bare $SiO_2$ were used. Any materials used for coating were allowed to deposit until a stable mass was reached (e.g., for five minutes) followed by five minutes of rinsing with buffer between each layer; (1) PEI or PSS, (2) nucleic acid and (3) the dye. After deposition, the film was rinsed with buffer for ten minutes. If the adsorbed mass returned to near the form immediately prior to the addition of the dye, then remained stable, the binding was characterized as reversible. Binding was characterized as irreversible if the mass remained constant after rinsing or leveled off at a substantially higher value than before the dye was added. Results are shown in Table 4.

TABLE 4

Summary of QCM-D binding study for three dyes

| | Ethidium Bromide | DAST | DANPY-1 |
|---|---|---|---|
| dsDNA | Irreversible | None | Irreversible |
| ssDNA | Binding. Inconclusive whether reversible. | Irreversible | Irreversible |
| PSS | Irreversible. Much more binding than DANPY or DAST | Partially reversible? | Reversible |
| tRNA | None/slight | Reversible | Irreversible |
| $SiO_2$ | Irreversible | Reversible | Reversible |

According to Table 4 above, binding of DANPY-1 was irreversible to all three nucleic acids tested in this example under the conditions described, DANPY-1 did not bind strongly to either of the control surfaces. DAST did not interact strongly with ds DNA or tRNA, but interacted strongly with PSS and ssDNA. Ethidium bromide did show superior binding to ds DNA compared to ssDNA or tRNA, but also bound to both control surfaces. Therefore, DANPY-1 may show higher specificity for nucleic acids, although not necessarily dsDNA or ssDNA compared to ethidium bromide.

The invention claimed is:

1. A method of staining a cell, the method comprising:
combining a compound and the cell comprising a nucleic acid molecule to form a complex including the compound and the nucleic acid molecule, thereby staining the cell; and
detecting the complex including the compound and the nucleic acid molecule,
wherein the compound has the genera formula (I):

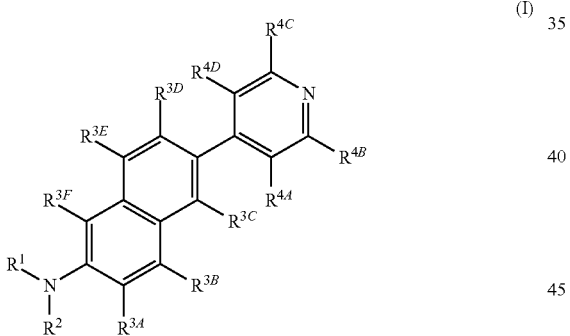

(I)

wherein
each of $R^1$ and $R^2$ are independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl,
or wherein $R^1$ and $R^2$ are joined together to form a substituted or unsubstituted cycloalkyl, substituted or unsubstituted heterocycloalkyl, substituted or unsubstituted aryl, or substituted or unsubstituted heteroaryl;
each of $R^{3A}$, $R^{3B}$, $R^{3C}$, $R^{3D}$, $R^{3E}$, $R^{3F}$, $R^{4A}$, $R^{4B}$, $R^{4C}$, and $R^{4D}$ are independently selected from the group consisting of hydrogen, a halide, —OH, —$NH_2$, —CN, —SH, —$NO_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl;
and salts and isomers thereof;
or the general formula (II):

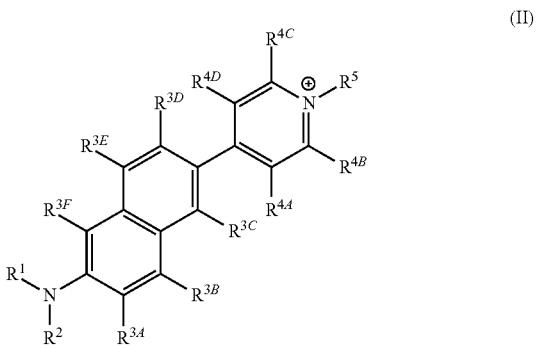

(II)

wherein
each of $R^1$ and $R^2$ are independently selected from the group consisting of hydrogen, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl,
or wherein $R^1$ and $R^2$ are joined together to form a substituted or unsubstituted cycloalkyl, substituted or unsubstituted heterocycloalkyl, substituted or unsubstituted aryl, or substituted or unsubstituted heteroaryl;
each of $R^{3A}$, $R^{3B}$, $R^{3C}$, $R^{3D}$, $R^{3E}$, $R^{3F}$, $R^{4A}$, $R^{4B}$, $R^{4C}$, and $R^{4D}$ are independently selected from the group consisting of hydrogen, a halide, —OH, —$NH_2$, —CN, —SH, —$NO_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl;
$R^5$ is selected from the group consisting of a halide, —CN, —$NO_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl;
and salts and isomers thereof.

2. The method of claim 1, further comprising detecting the complex including the compound and the nucleic acid molecule.

3. The method of claim 1, wherein
the compound has the genera formula (I), wherein
each of $R^1$ and $R^2$ are independently selected from the group consisting of hydrogen, substituted or unsubstituted methyl, ethyl, propyl, isopropyl, isobutyl, sec-butyl, tert-butyl, pentyl, isopentyl, hexyl, heptyl, octyl, nonyl, decyl, substituted butyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein $R^1$ and $R^2$ are joined together to form a substituted or unsubstituted heterocycloalkyl or substituted or unsubstituted heteroaryl;

each of $R^{3A}$, $R^{3B}$, $R^{3C}$, $R^{3D}$, $R^{3E}$ and $R^{3F}$ are independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl;

$R^{4A}$, $R^{4D}$ are hydrogen;

each of $R^{4B}$ and $R^{4C}$ are independently hydrogen or —CN;

and salts and isomers thereof;

or the general formula (II):
wherein
each of $R^1$ and $R^2$ are independently selected from the group consisting of hydrogen, substituted or unsubstituted methyl, ethyl, propyl, isopropyl, isobutyl, sec-butyl, tert-butyl, pentyl, isopentyl, hexyl, heptyl, octyl, nonyl, decyl, substituted butyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl, or wherein $R^1$ and $R^2$ are joined together to form a substituted or unsubstituted heterocycloalkyl or substituted or unsubstituted heteroaryl;

each of $R^{3A}$, $R^{3B}$, $R^{3C}$, $R^{3D}$, $R^{3E}$ and $R^{3F}$ are independently selected from the group consisting of hydrogen, a halide, —OH, —NH$_2$, —CN, —SH, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl;

$R^{4A}$, $R^{4D}$ are hydrogen;

each of $R^{4B}$ and $R^{4C}$ are independently hydrogen or —CN;

$R^5$ is selected from the group consisting of a halide, —CN, —NO$_2$, substituted or unsubstituted alkyl, substituted or unsubstituted heteroalkyl, substituted or unsubstituted acyl, substituted or unsubstituted alkoxy, substituted or unsubstituted cycloalkyl, substituted or unsubstituted heterocycloalkyl, substituted or unsubstituted aryl, and substituted or unsubstituted heteroaryl;

and salts and isomers thereof;

provided that
when $R^{4A}$, $R^{4B}$, $R^{4C}$ and $R^{4D}$ are hydrogen, $R^1$ and $R^2$ are not phenyl.

4. The method of claim 1, wherein each of $R^1$ and $R^2$ are independently selected from substituted or unsubstituted methyl, ethyl, propyl, isopropyl, isobutyl, sec-butyl, tert-butyl, pentyl, isopentyl, hexyl, heptyl, octyl, nonyl, decyl, substituted butyl, unsubstituted acyl, substituted or unsubstituted alkoxy, unsubstituted heteroalkyl, unsubstituted cycloalkyl, unsubstituted heterocycloalkyl, unsubstituted aryl, substituted or unsubstituted aryl, and unsubstituted heteroaryl.

5. The method of claim 1, wherein each of $R^1$ and $R^2$ are unsubstituted methyl, ethyl, propyl, isopropyl, isobutyl, sec-butyl, tert-butyl, pentyl, isopentyl, hexyl, heptyl, octyl, nonyl, decyl, substituted butyl, or wherein $R^1$ and $R^2$ are joined together to form a substituted or unsubstituted heterocycloalkyl, substituted or unsubstituted aryl, or substituted or unsubstituted heteroaryl.

6. The method of claim 1, wherein $R^5$ is fluorinated alkyl, fluorinated heteroalkyl, fluorinated acyl, fluorinated alkoxy, fluorinated cycloalkyl, fluorinated heterocycloalkyl, fluorinated aryl, or fluorinated heteroaryl.

7. The method of claim 1, wherein $R^5$ is unsubstituted $C_1$-$C_{10}$ alkyl.

8. The method of claim 1, wherein $R^5$ is selected from the group consisting of substituted or unsubstituted alkyl, substituted or unsubstituted acyl, substituted or unsubstituted alkoxy, and substituted or unsubstituted aryl.

9. The method of claim 1, wherein the compound of general formula (II) comprises a salt including a counterion selected from the group consisting of a halide, acetate, trifluoroacetate and tosylate.

10. The method of claim 1, having any one of the following formulas:

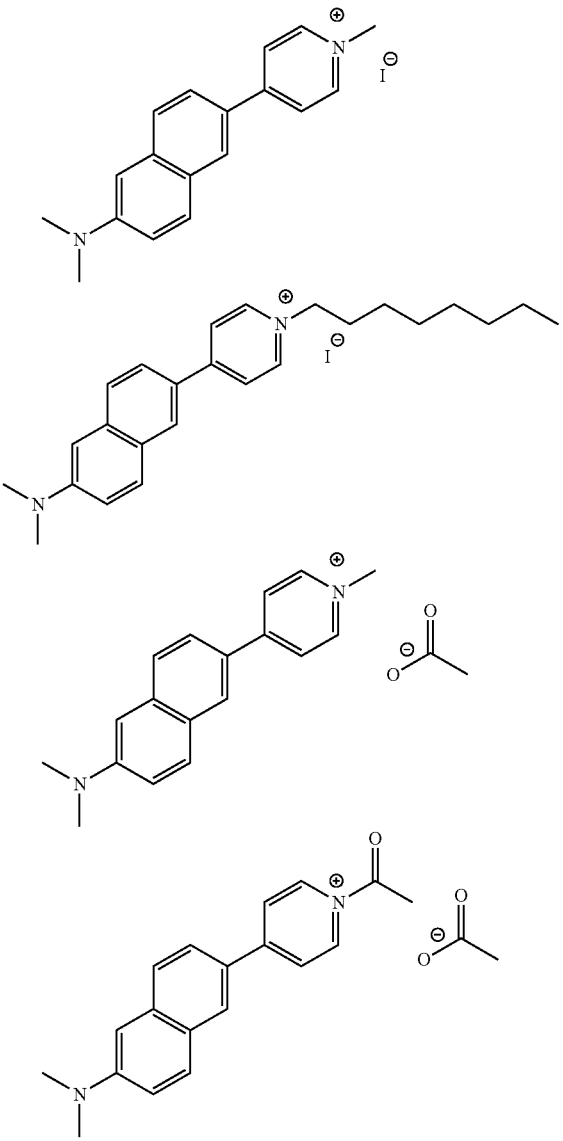

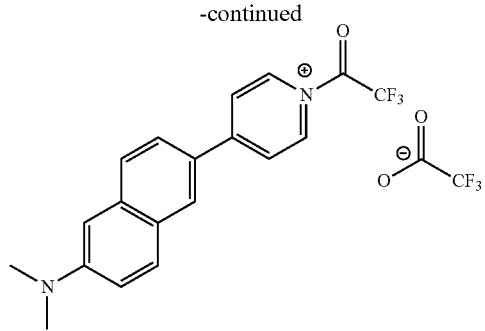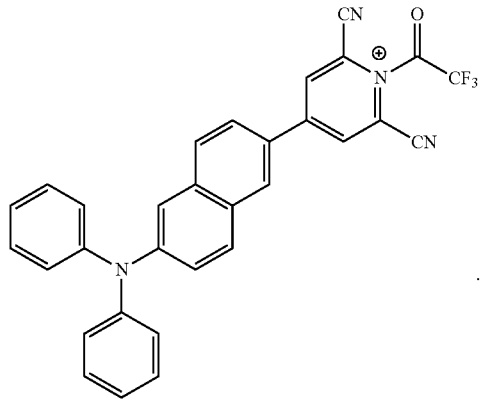 [SMILES: N#Cc1cc(-c2ccc3cc(N(c4ccccc4)c4ccccc4)ccc3c2)cc(C#N)[n+]1C(=O)C(F)(F)F]
* * * * *